(12) United States Patent
Desai et al.

(10) Patent No.: US 8,491,872 B2
(45) Date of Patent: Jul. 23, 2013

(54) CINNAMIC ACID-BASED OLIGOMERS AND USES THEREOF

(75) Inventors: Umesh R. Desai, Glen Allen, VA (US); Brian L. Henry, Pittsburgh, PA (US); Aiye Liang, North Charleston, SC (US); Jay Thakkar, Denver, CO (US); John B. Mangrum, Richmond, VA (US); Ivo Torres Filho, Glen Allen, VA (US); Bruce D. Spiess, Manakin-Sabot, VA (US); Masahiro Sakagami, Richmond, VA (US); Bhawana Saluja, N. Bethesda, MD (US)

(73) Assignee: Virginia Commonwealth University, Richmond, VA (US)

( * ) Notice: Subject to any disclaimer, the term of this patent is extended or adjusted under 35 U.S.C. 154(b) by 117 days.

(21) Appl. No.: 13/057,374

(22) PCT Filed: Aug. 4, 2009

(86) PCT No.: PCT/US2009/052684
§ 371 (c)(1),
(2), (4) Date: Sep. 15, 2011

(87) PCT Pub. No.: WO2010/027594
PCT Pub. Date: Mar. 11, 2010

(65) Prior Publication Data
US 2012/0027691 A1  Feb. 2, 2012

Related U.S. Application Data

(60) Provisional application No. 61/085,916, filed on Aug. 4, 2008, provisional application No. 61/091,487, filed on Aug. 25, 2008.

(51) Int. Cl.
| | | |
|---|---|---|
| *A61P 7/02* | (2006.01) | |
| *A61P 29/00* | (2006.01) | |
| *A61P 11/00* | (2006.01) | |
| *A61K 31/185* | (2006.01) | |
| *A61K 31/343* | (2006.01) | |
| *A61K 31/255* | (2006.01) | |
| *C07C 305/24* | (2006.01) | |
| *C07D 307/80* | (2006.01) | |
| *C07D 307/84* | (2006.01) | |
| *C07D 407/14* | (2006.01) | |

(52) U.S. Cl.
USPC ............. 424/45; 514/469; 514/518; 549/468; 562/36

(58) Field of Classification Search
None
See application file for complete search history.

(56) References Cited

FOREIGN PATENT DOCUMENTS

| | | |
|---|---|---|
| JP | 2003-73392 | 3/2003 |
| KR | 10-2006-0033071 | 4/2006 |
| WO | 2008/062466 | 5/2008 |

OTHER PUBLICATIONS

Zhang et al., caplus an 1993:212590.*
Verghese et al.; "First steps in the direction of synthetic, allosteric, direct inhibitors of thrombin and factor Xa"; Bioorganic & Medicinal Chemistry Letters, vol. 19, 2009, pp. 4126-4129.
Monien et al.; "Novel chemo-enzymatic oligomers of cinnamic acids as direct and indirect inhibitors of coagulation proteinases"; Bioorganic & Medicinal Chemistry, vol. 14, 2006, pp. 7988-7998.
Henry et al.; "A Novel Allosteric Pathway of Thrombin Inhibition"; The Journal of Biological Chemistry, vol. 282, No. 44, Nov. 2, 2007, pp. 31891-31899.
Henry et al.; "Interaction of Antithrombin with Sulfated, Low Molecular Weight Lignins"; The Journal of Biological Chemistry, vol. 284, 2009, pp. 1-12.
Henry et al.; "Characterization of the plasma and blood anticoagulant potential of structurally and mechanistically novel oligomers of 4-hydroxycinnamic acids"; Blood Coagulation and Fibrinolysis, vol. 20, No. 1, 2009, pp. 27-35.
Oudgenoeg et al.; "Horseradish Peroxidase-catalyzed Oligomerization of Ferulic Acid on a Template of a Tyrosine-containing Tripeptide"; The Journal of Biological Chemistry, vol. 277, No. 24, Jun. 14, 2002, pp. 21332-21340.

* cited by examiner

*Primary Examiner* — Sun Jae Loewe
(74) *Attorney, Agent, or Firm* — Whitham Curtis Christofferson & Cook, PC

(57) ABSTRACT

Cinnamic acid-based oligomers and therapeutic uses thereof are provided. The oligomers are used as anti-inflammation agents, inhibitors of elastase and anti-oxidants, and in some cases (e.g. the treatment of lung disorders such as lung cancer) all three activities are simultaneously beneficial. Subsets of the oligomers (e.g. β-O4 and β-5 trimers and tetramers) are used as anticoagulants.

6 Claims, 9 Drawing Sheets

CINNAMIC ACID-BASED OLIGOMERS AND USES THEREOF

CROSS-REFERENCE TO RELATED APPLICATIONS

This application is a national stage filing of PCT/US2009/052684 filed Aug. 4, 2009, which claims priority to U.S. Ser. No. 61/091,487 filed Aug. 25, 2009 and U.S. Ser. No. 61/085,916 filed Aug. 4, 2009.

BACKGROUND OF THE INVENTION

1. Field of the Invention

The invention generally relates to cinnamic acid-based oligomers and therapeutic uses thereof. In particular, the invention provides cinnamic acid-based oligomers, and subsets thereof, for use as anti-coagulants, anti-inflammation agents, inhibitors of elastase and anti-oxidants.

2. Background of the Invention

1) Coagulation: Coagulation is a defense mechanism. It prevents excessive loss of blood following an injury as well as prevents infiltration of microbes. Yet, aberrant clotting is detrimental. Numerous disease states, including deep vein thrombosis and pulmonary embolism, arise due to inappropriate clotting. Inhibitors of thrombin and factor Xa have been primarily used to control inadvertent and inappropriate clotting. These include heparins (unfractionated heparin, low molecular weight heparin and fondaparinux) and coumarin derivatives (warfarin). Both of these agents suffer from major problems, e.g., enhanced bleeding risk, unpredictable response, etc. Newer agents that possess thrombin and factor Xa inhibition properties are actively being pursued.

Inhibitors of thrombin and factor Xa can be of two types—direct inhibitors and indirect inhibitors. Heparin are indirect inhibitors of thrombin and factor Xa, while hirudin, argatroban and rivaroxaban, two newer anticoagulants, are direct inhibitors. Direct inhibition of coagulation enzymes has been thought to be a better alternative, which promises to offer the important advantage of inhibition of both circulating and clot-bound thrombin. A prototypic member in this class of inhibitors is hirudin, which targets the active-site and exosite I of thrombin, and several derivatives of this peptide are now clinically available. Intensive efforts are also being made to develop the first orally bio-available direct thrombin inhibitor. These are small molecule pro-drugs that target the active site of these enzymes. However, challenges with these molecules include establishing enzyme binding affinity that is not associated with excessive bleeding, achieving inhibition of both clot-bound and unbound proteinases, and avoiding liver toxicity. Thus, there is an ongoing need for the development of alternative anti-coagulation agents.

2) Inflammation: Neutrophils play a critical role in host defense against invading pathogens. Pro-inflammatory mediators and chemotactic attractants activate neutrophils to engulf pathogens by phagocytosis. Neutrophil elastase is a potent serine protease that is released upon neutrophil activation in response to inflammatory signals that can destroy pathogens.

Neutrophil elastase cleaves and inactivates α1-proteinase inhibitor, tissue inhibitor of metalloproteinase, and complement fragment C3. It also appears that neutrophil elastase mimics the action of endogenous metalloproteinases directly activating degranulation and effectively bypassing the normal signal transduction pathways necessary for degranulation. Neutrophils constitutively express all membrane associated components of the nicotinamide-adenine-dinucleotide phosphate (NADPH) oxidase complex required to produce super oxide anion during a respiratory burst. Activation of neutrophils via chemotaxin receptors results in super oxide anion production. In the presence of low pH, super oxide anion is converted by super oxide dismutase into hydrogen peroxide and hydroxyl radicals which have intense anti-microbial properties. This pathway may contribute to the killing of protozoan, fungi and helminths.

Although beneficial for host defense against pathogens, aberrant activation of neutrophils and neutrophil elastase can also cause problems for its host and result in severe tissue damage. Neutrophil elastase is one of the most destructive enzymes in the body, with the capability of degrading extracellular matrix proteins (including collagens, proteoglycans, fibronectins, platelet receptors, complement receptors, thrombomodulin, lung surfactants and cadherins) and key plasma proteins (including coagulation and complement factors, immunoglobulins, several proteases and protease inhibitors). Under physiological conditions, endogenous protease inhibitors, such as α1-antitrypsin, tightly regulate the activity of neutrophil elastase. However, at inflammatory sites, neutrophil elastase is able to evade regulation, and once unregulated it can induce the release of pro-inflammatory cytokines, such as interleukin-6 and interleukin-8, leading to acute lung injury. Neutrophil elastase induction of IL-8 expression in bronchial epithelial cells, injures bronchial endothelial cells in part through the release of platelet activating factor (PAF), increases endothelial cell permeability, induces endothelial cell apoptosis, and degranulates eosinophils.

Acute lung tissue damage from aberrant neutrophil activation can lead to emphysema, chronic obstructive pulmonary disease, cystic fibrosis, and adult respiratory distress syndrome. Examples of non-respiratory diseases involving the inflammatory activity of neutrophil elastase are chronic inflammatory bowel disease, rheumatoid arthritis, and septic shock. There is a critical need to provide treatments for aberrant inflammation, elastase activity and oxidation.

SUMMARY OF THE INVENTION

Three general classes of sulfated, hydroxylated oligomers derived from cinnamic acid are disclosed herein. One class of oligomers is derived from caffeic acid (CA), one from ferulic acid (FA) and one from sinapic acid (SA), and the classes are referred to herein as CDSO3, FDSO3 and SDSO3, respectively. CDSO3s, FDSO3s and SDSO3s in general display several interesting properties: 1) They are potent inhibitors of thrombin and factor Xa, two enzymes of the coagulation cascade. By inhibiting these enzymes, the three classes display anticoagulant activity. 2) They act as potent anti-inflammatory agents. 3) They inhibit neutrophil elastase. 4) They possess anti-oxidant activity. In combination, the oligomers are suitable for use in treating diseases and conditions characterized by aberrant coagulation, inflammation, unwanted elastase activity and/or oxidation, for example, lung disorder such as pulmonary embolism and lung diseases such as emphysema. More specifically, subsets of these oligomers, in particular, β-O4 and β-5 trimers and tetramers, display the ability to directly inhibit both factor Xa and thrombin and hence are powerful anticoagulants.

It is an object of this invention to provide cinnamic acid-based oligomers with a structure as represented in Formula 1.

Formula 1

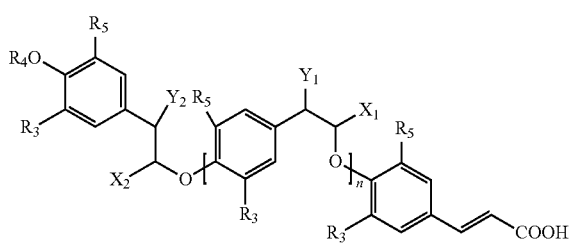

In Formula 1, $R_3$=—OH or —OCH$_3$, $R_4$=—H or —SO$_3^-$M$^+$ where M$^+$=an organic or inorganic cation; $R_5$=—H or —OCH$_3$; $X_1$ and $X_2$=—H or —COOH; $Y_1$ and $Y_2$=—H or —OH or —SO$_3^-$M$^+$ where M$^+$=H$^+$ or an organic or inorganic cation; and n=1 or 2; and linkages between monomers of the cinnamic acid-based oligomer are β-O4 linkages. The cinnamic acid-based oligomers also include all possible stereo-isomers of Formula 1. In some embodiments of the invention, the cinnamic acid-based oligomer is a trimer, for example

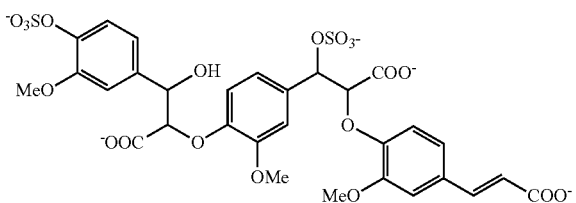

where the negative charges are within ionic bonding distance of H$^+$ or an organic or inorganic cation; whereas in other embodiments, the cinnamic acid-based oligomer is a tetramer, for example,

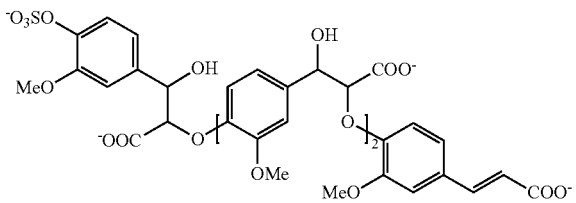

where the negative charges are within ionic bonding distance of H$^+$ or an organic or inorganic cation.

The invention also provides cinnamic acid-based oligomers with a structure as represented in Formula 2.

Formula 2

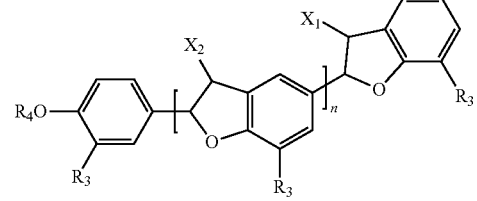

In Formula 2, $R_3$=—OH or —OCH$_3$; $R_4$=—H or —SO$_3^-$M$^+$ in which M$^+$=H$^+$ or an organic or inorganic cation; $X_1$, $X_2$=—H or —COOH; and n=1 or 2; and linkages between monomers of the cinnamic acid-based oligomer are β-5 linkages. The cinnamic acid-based oligomers also include all possible stereo-isomers of Formula 2. In some embodiments of the invention, the cinnamic acid-based oligomer is a trimer, for example,

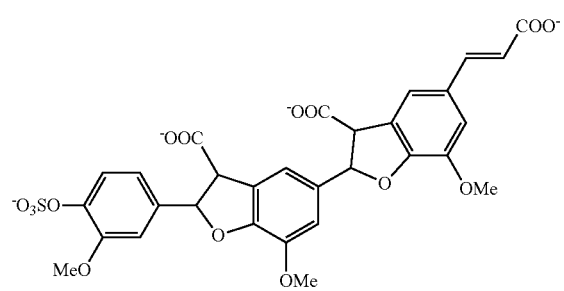

where the negative charges are within ionic bonding distance of H$^+$ or an organic or inorganic cation; whereas in other embodiments, the cinnamic acid-based oligomer is a tetramer, for example,

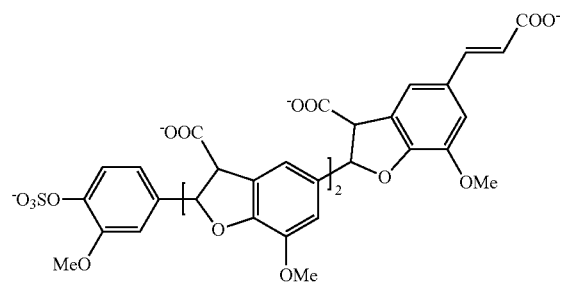

where the negative charges are within ionic bonding distance of H$^+$ or an organic or inorganic cation.

The invention also provides a method of inducing anti-coagulation in a patient in need thereof. The method comprises the step of comprising administering to the patient i) one or more cinnamic acid-based oligomers with a structure as represented in Formula 1

Formula 1

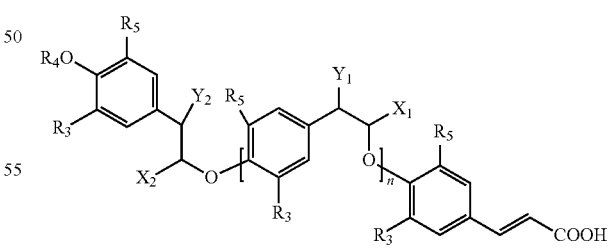

where $R_3$=—OH or —OCH$_3$, $R_4$=—H or —SO$_3^-$M$^+$ where M$^+$=an organic or inorganic cation; $R_5$=—H or —OCH$_3$; $X_1$ and $X_2$=—H or —COOH; $Y_1$ and $Y_2$=—H or —OH or —SO$_3^-$M$^+$ where M$^+$=H$^+$ or an organic or inorganic cation; and n=1 or 2; and linkages between monomers of the cinnamic acid-based oligomer are β-O4 linkages; or ii) one or more cinnamic acid-based oligomers with a structure as represented in Formula 2

Formula 2

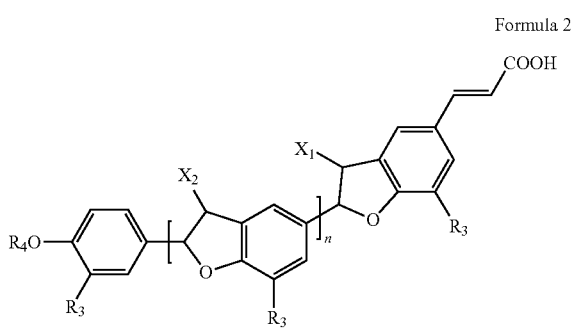

wherein $R_3 =$ —OH or —OCH$_3$, $R_4 =$ —H or —SO$_3^-$M$^+$ in which M$^+$=H$^+$ or an organic or inorganic cation; $X_1$, $X_2 =$ —H or —COOH; and n=1 or 2; and linkages between monomers of the cinnamic acid-based oligomer are β-5 linkages; or any stereo-isomer of Formula 1 or 2.

The invention also provides a method of treating inflammation, inhibiting elastase and/or suppressing oxidation in a patient in need thereof. The method comprises the step of administering to the patient one or more cinnamic acid-based oligomers of structure $$(OH)_x\sim(C)_y\sim(SO_3^-)_z\cdot M^+{}_z \qquad \text{Formula 3}$$

where C is a cinnamic acid-based monomeric unit and y ranges from 3 to 20; OH is a hydroxyl group and x ranges from 1 to 20; SO$_3^-$ is a sulfate group and M$^+$ is an organic or inorganic cation and z ranges from 1 to 20. In some embodiments of the invention, the cinnamic acid-based monomeric unit is a caffeic acid-based monomeric unit, or a ferulic acid based monomeric unit or a sinapic acid based monomeric unit.

The invention also provides a method of treating lung disorders involving inflammation, elastase activity or oxidation, in a patient in need thereof. The method includes the step of administering to the patient one or more cinnamic acid-based oligomers of structure $$(OH)_x\sim(C)_y\sim(SO_3^-)_z\cdot M^+{}_z \qquad \text{Formula 3}$$

where C is a cinnamic acid-based monomeric unit and y ranges from 3 to 20; OH is a hydroxyl group and x ranges from 1 to 20; SO$_3^-$ is a sulfate group and M$^+$ is an organic or inorganic cation and z ranges from 1 to 20. In some embodiments, the cinnamic acid-based monomeric unit is a caffeic acid-based monomeric unit, a ferulic acid based monomeric unit or a sinapic acid based monomeric unit. Lung disorders that are so treated include emphysema, acute lung injury, chronic obstructive pulmonary disease. In some embodiments, the step of administering is carried out via inhalation of an aerosol comprising the one or more cinnamic acid-based oligomers.

The invention further provides cinnamic acid-based oligomers, wherein the cinnamic acid-based oligomers are made by the steps of: i) oxidizing a plurality of cinnamic acid-based monomers to form cinnamic acid-based monomeric free radicals; ii) allowing the cinnamic acid-based monomeric free radicals to polymerize, forming a cinnamic acid-based oligomer; and iii) sulfating the cinnamic acid-based oligomer. The cinnamic acid-based monomers are selected from caffeic acid monomers, ferulic acid monomers, and sinapic acid monomers.

DETAILED DESCRIPTION

Figure 1:
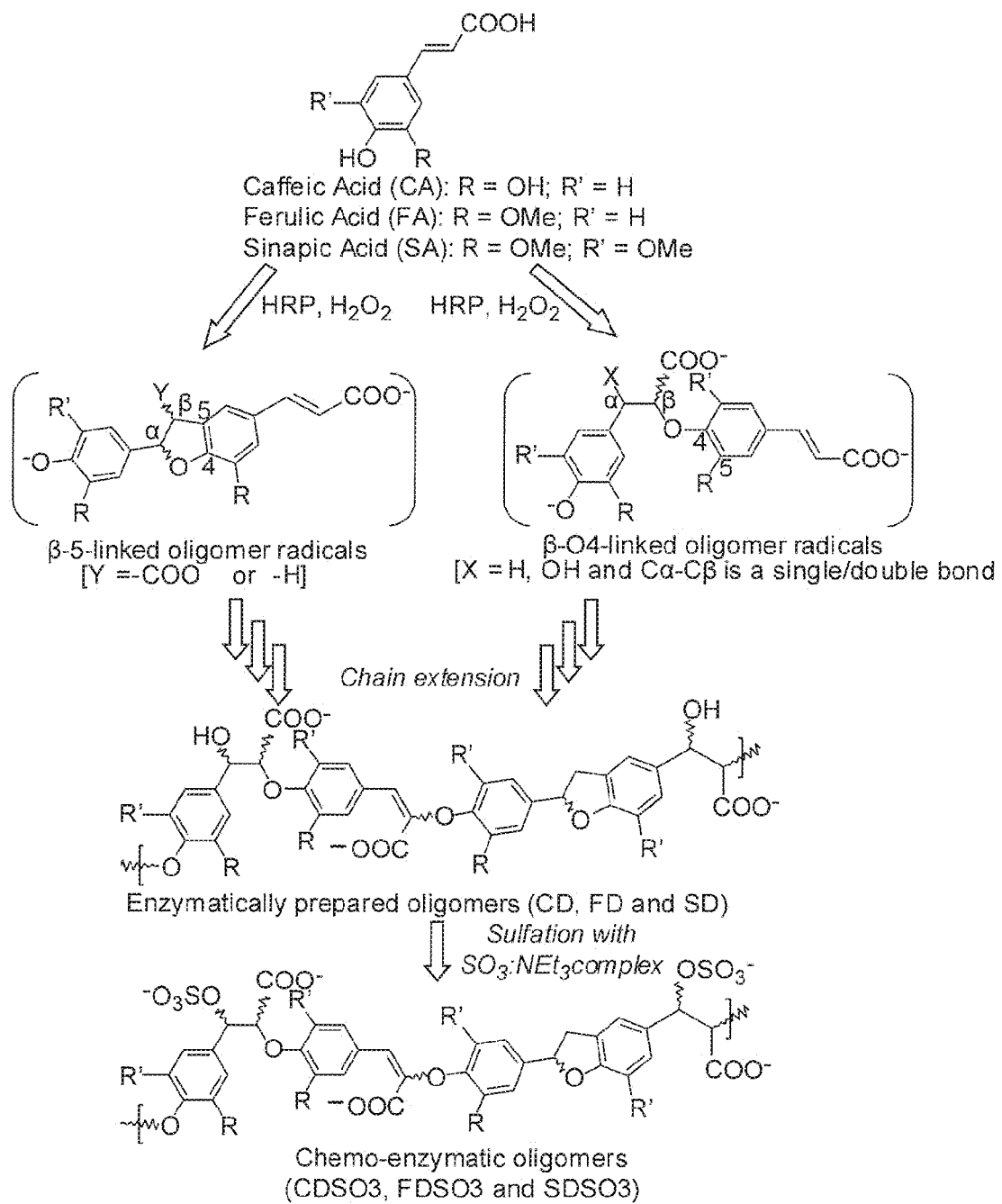
FIG. 1. Schematic illustration of the preparation of cinnamic acid-based oligomers.

Three general classes of sulfated, hydroxylated oligomers derived from cinnamic acid are disclosed herein. One class of oligomers is derived from caffeic acid (CA), one from ferulic acid (FA) and one from sinapic acid (SA), and are referred to herein as CDSO3 (CDS), FDSO3 (or FDS) and SDSO3 (or SDS), respectively. Subsets of these oligomers, in particular, β-O4 and β-5 trimers and tetramers, are powerful anticoagulants and display the ability to directly inhibit both factor Xa and thrombin. As such, these agents are useful as replacements for or, in some cases, to be used with, currently known anticoagulants such as heparin. The fact that these oligomers are capable of direct inhibition of factor Xa and thrombin implies that the deleterious side effects experienced by patients treated with these agents are expected to be fewer.

In addition, CDSO3s, FDSO3s and SDSO3s in general display additional three interesting properties: they act as potent anti-inflammatory agents; they inhibit elastase enzyme, and they are anti-oxidants. As such, the oligomers are suitable for use in treating diseases and conditions characterized by inflammation, unwanted elastase activity and oxidation. For example, lung diseases such as emphysema, acute lung injury (ALI), and chronic obstructive pulmonary disease (COPD), may be treated using these oligomers. Use of these agents is particularly advantageous since all three activities are displayed by a single oligomer, thus eliminating the need to administer multiple medicaments to a patient in order to achieve treatment of all three disease-related symptoms.

In order to produce the compounds of the invention, three cinnamic acid derivatives, caffeic acid, ferulic acid and sinapic acid, were chosen for homo-polymerization primarily due to their ability to hydrogen bond, form ionic interactions and undergo sulfation. The oligomers (which may be referred to as "synthetic lignins" or "lignin carboxylates" or sulfated low molecular weight lignins due to their lignin-like structure) were prepared in good yields through chemo-enzymatic oxidative coupling of the 4-hydroxycinnamic acids. Horseradish peroxidase (HRP)-catalyzed oxidation of these monomers generates radical intermediates (see FIG. 1), which couple with monomers to give dimeric units with at least four types of inter-monomer linkages, including β-O-4- and β-5- linkages. These units undergo chain extension with radical intermediates to give a group of oligomers, referred to as dehydropolymers (DHPs). Simultaneously, side reactions, such as decarboxylation, may occur to give variant oligomers, resulting in heterogeneous, polydisperse oligomer preparations. These variations introduce significant heterogeneity and complexity in the macromolecules, thereby generating high structural diversity. The DHPs exhibit the ability to prolong activated thromboplastin and prothrombin time (APTT and PT, respectively) with approximately equal potency as LMWH. Further, the DHPs inhibit factor Xa and thrombin in an antithrombin-dependent and -independent manner suggesting an interesting dual inhibition approach.

The invention thus provides oligomers (or low molecular weight polymers) comprising monomeric subunits based on cinnamic acid-based monomers such as caffeic acid, ferulic acid or sinapic acid, or combinations thereof (i.e. in some embodiments, the starting material is a mixture of two or more of caffeic acid, ferulic acid and sinapic acid, or other cinnamic acid-based monomer such as 3,4,5-trihydroxycinnamic acid, 2,4,6-trihydroxycinnamic acid, and their alkylated or acylated derivatives. The oligomers are formed using an enzymatic-chemical procedure according to which the monomers are first oxidized (e.g. by treatment with HRP). Oxidation of the monomers results in production of free radical species which then interact with each other and/or with unoxidized monomers to form extended oligomer chains. Linkages between the monomers are typically of several different types, examples of which include but are not limited to β-O-4-, β-5-, β-β-, and 5-5. During oligomer formation (extension, elongation, etc.) side reactions such as decarboxylation, dehydration or hydrolysis may also occur, resulting in increased heterogeneity of the oligomers. Oxidation and elongation are allowed to proceed, for example, until the average molecular weight of the oligomeric mixture reaches 3000-5000 (as measured by size exclusion chromatography). Generally, the number of monomeric units in an oligomer ranges from about 2 to about 20, and usually from about 4 to about 15, i.e. the number of monomers may be, for example, 2, 3, 4, 5, 6, 7, 8, 9, 10, 11, 12, 13, 14, 15, 16, 17, 18, 19, 20 or even higher. In some embodiments, the oligomers are 3-mers or 4-mers. After oligomer formation, the oligomeric mixture is sulfated using one or more methods known to those of skill in the art e.g. using an Et$_3$N:SO$_3$ complex. Sulfation is allowed to proceed to any desired extent, typically so that each available hydroxyl group is sulfated. Thus, the oligomers of the invention may contain 0-3 sulfate groups per monomer, and possibly 1 or more sulfate group per oligomer, with a typical ratio being approximately 1 sulfate group for every 2-3 monomers in an oligomer. The sulfated oligomers may also generally contain one or more hydroxyl groups per monomer in an oligomer, e.g. about 1 hydroxyl for each 2-3 monomers in an oligomer. The final products (sulfated, hydroxylated oligomers of cinnamic acid-based monomers) may be referred to herein as CDSO3s (if derived from caffeic acid), FDSO3s (if derived from ferulic acid) or SDSO3s (if derived from sinapic acid).

The oligomers may be schematically represented as follows:

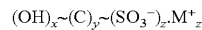

$$(OH)_x\sim(C)_y\sim(SO_3^-)_z \cdot M^+_z \quad \text{Formula 3}$$

where
C represents a cinnamic acid-based monomeric unit of the oligomer, and y ranges from 3 to 20;
OH is a hydroxyl group and x ranges from 1 to 20;
SO$_3^-$ is a sulfate group, M$^+$ is an organic or inorganic cation (e.g. Na$^+$, K$^+$, NH$_4^+$, various amines, etc.), z ranges from 1 to 20, and "~" represents a bond between a monomer of the oligomer and a hydroxyl or sulfate, with the caveat that at least one monomer of the oligomer is bonded to at least one hydroxyl and at least one monomer of the oligomer is bonded to at least one sulfate (i.e. the oligomer comprises at least one hydroxyl and at least one sulfate). Hydroxyl-bearing and sulfate-bearing monomers may be the same monomer (i.e. one monomer bears at least one hydroxyl and at least one sulfate); or hydroxyls and sulfates may be attached to different monomers (one monomer bears at least one hydroxyl and another monomer bears at least one sulfate); or the oligomer may comprise a mixture of these types of monomers. In addition, the oligomer may also include non-hydroxylated and non-sulfated monomers. In some embodiments, C is based on or derived from caffeic acid; in other embodiments, C is based on or derived from ferulic acid; in yet other embodiments, C is based on or derived from sinapic acid, the structures of each of which are shown in FIG. 1. Linkages between the monomeric units may be any of several different types, as described above.

Prior to use in the methods described herein, the oligomers are treated to eliminate unwanted chemical reactants, i.e. they are isolated and/or substantially purified by methods known to those of skill in the art, e.g. by column chromatography, dialysis, etc. and re-suspended in a physiologically compatible buffer or carrier. In some embodiments, the oligomers may be fractionated (e.g. as described in the Examples section below) in order to select oligomers of a particular size range, molecular weight, composition, activity, etc. Depending on the use of the preparation, the final material that is used in a method may comprise one or more types of oligomers, i.e. may comprise only a single species of oligomer, or may comprise a plurality of oligomer species.

In one embodiment of the invention, the cinnamic-acid based oligomers of the invention are used to treat disorders characterized or caused by or involving both acute and/or chronic inflammation, activity of the elastase enzyme (e.g. neutrophil increase and neutrophil secretion of elastase) and/or oxidation, examples of which are described in detail below and include, but are not limited to, various lung disorders. While agents capable of treating each of these symptoms exist, the oligomers of the invention advantageously possess all three activities (anti-inflammatory, anti-elastase, and anti-oxidant). While any disease or disorder involving any one, or two, or all three, of these symptoms may be treated using the oligomers, particular efficacy has been shown in treating lung disorders, especially when treated by inhalation therapy. Examples of lung disorders that may be treated using the oligomers include but are not limited to emphysema, acute lung injury (ALI), chronic obstructive pulmonary disease (COPD), chronic bronchitis, pulmonary edema, asthma, diffuse panbronchiolitis, alveolar ectasia, bronchietasis, bacterial pneumonia, respiratory distress syndrome, sinusitis, and various lung diseases caused by inhalation of noxious agents e.g. smoke, various particulates (e.g. pollutants, chemicals, asbestos fibers, etc.). In one embodiment, the oligomers are used to treat lung diseases such as those caused by smoking tobacco products (e.g. cigarettes, cigars, etc.) or other substances (marijuana, etc.). In one embodiment, for the treatment of lung disorders, the oligomers are administered locally to the lung by inhalation. The invention thus also encompasses pharmaceutical formulations that are suitable for administration by inhalation. Generally, oligomers with molecular weights in the range of from about 1,000 to about 4,000 are considered to be advantageous for inhalation drug delivery. The oligomers of the invention are especially suitable for local disease treatment in the lung by virtue of their long residence time within the lung and low systemic bioavailability. Moreover, unlike peptides and proteins, the oligomers are likely to be less susceptible to metabolic degradation within the lung, or elsewhere within the body when delivered to other sites or systemically. The oligomers are thus advantageous for both local and systemic delivery. Inhalation formulations are known to those of skill in the art, and include, for example, a physiological carrier and a suitable propellant or mechanism for delivering an aerosolized form of the oligomers (e.g. a mist, powder, etc.) to the lung. However, in some instances, other types of administration may also be employed (e.g. by injection, orally, nasally, etc.).

In one embodiment of the invention, specific cinnamic-acid based oligomers of the invention are used as anticoagulants. For this purpose, in particular, β-O4 and β-5 trimers and tetramers sulfated at one or more positions and hydroxylated at one or more positions are preferred. In particular, sulfated and hydroxylated β-O4 trimers and tetramers have a generic structure as follows:

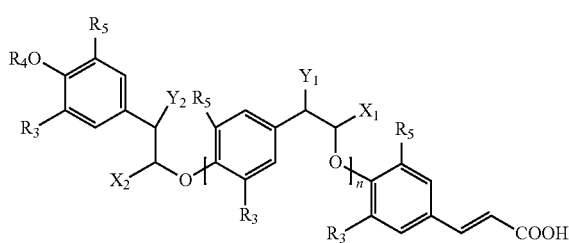

Formula 1 wherein
$R_3$=—OH or —OCH$_3$,
$R_4$=—H or —SO$_3^-$M$^+$ in which M$^+$=an inorganic cation (e.g. Na$^+$, K$^+$, etc.) or any organic cation (e.g., NH$_4^+$, various amines, etc.);
$R_5$=—H or —OCH$_3$;
$X_1$ and $X_2$=—H or —COOH;
$Y_1$ and $Y_2$=—H or —OH or —SO$_3^-$M$^+$ in which M$^+$=an inorganic cation (e.g., Na$^+$, K$^+$, etc.) or an organic cation (e.g., NH$_4^+$, various amines, etc.); and
n=1 or 2 (trimer and tetramer, respectively); as well as stereo-isomers (at one or more of any carbon atom) thereof.
Sulfated and hydroxylated β-5 trimers and tetramers have a generic structure as follows:

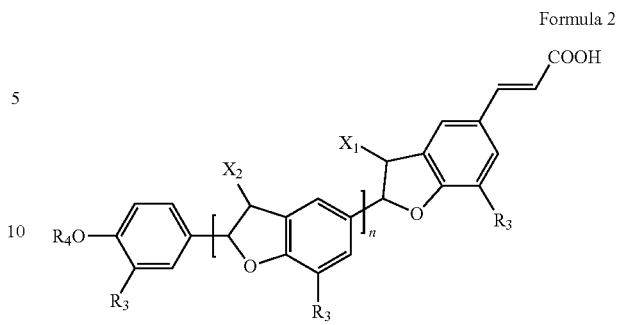

Formula 2 wherein
$R_3$=—OH or —OCH$_3$,
$R_4$=—H or —SO$_3^-$M$^+$ in which M$^+$=an inorganic cation (e.g. Na$^+$, K$^+$, etc.) or an organic cation (e.g., NH$_4^+$, various amines, etc.);
$X_1$, $X_2$=—H or —COOH; and
n=1 or 2 (trimer and tetramer, respectively); as well as stereoisomers (at one or more of any carbon atom) thereof.

In Formulas 1 and 2, individual monomers (monomeric units or subunits) of the oligomer are shown as separated by brackets, and the linkages (chemical bonds) between monomers are β-O4 (Formula 1) or β-5 (Formula 2).

The present invention provides compositions of the cinnamic acid-based oligomers, including compositions suitable for the treatment of disorders involving inflammation, activity of the elastase enzyme and/or oxidation, as well as anticoagulant compositions. The compositions include one or more isolated and/or substantially purified oligomers and a pharmacologically suitable carrier. The preparation of such compositions for therapeutic use is well known to those of skill in the art. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. In addition, the composition may contain other beneficial agents, e.g. other therapeutic agents, anesthetics, etc. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of oligomer(s) in the formulations may vary. However, in general, the amount in the formulations will be from about 1-99%. Patients to whom the oligomers are administered are generally mammals (although this need not always be the case), and include both humans and animals, i.e. veterinary applications are also contemplated.

The oligomer compositions (preparations) of the present invention may be administered by any of the many suitable means which are well known to those of skill in the art, including but not limited to by injection, inhalation, orally, intravaginally, intranasally, by ingestion of a food or probiotic product containing the oligomer(s), topically, as eye drops, via sprays, incorporated into dressings or bandages (e.g. lyophilized forms may be included directly in the dressing), etc. In some embodiments, depending on the condition being treated, the mode of administration may be topical, oral, by injection or by inhalation. In particular, pulmonary delivery may be carried out by inhalation using, for example, nebulizers, metered dose inhalers (MDIs), dry powder inhalers (PDIs), and the like, as will be understood by those of skill in the art. In addition, the compositions may be administered in conjunction with other treatment modalities such as substances that boost the immune system, various chemotherapeutic agents, antibiotic agents, and the like.

The amount of oligomer that is administered may vary somewhat from patient to patient and, as will be recognized by those of skill in the art, is generally determined in standard clinical trials. However, the amount will generally be in the range of from about 0.01 to about 100 mg/kg, and more specifically in the range of from about 0.1 to about 10 mg/kg. Those of skill in the art will recognize that while in some instances a complete cure may be achieved (i.e. the deleterious symptoms of disease may disappear altogether), this need not be the case in order for a patient to benefit from administration of the oligomers. Partial amelioration of symptoms is also envisioned and can be of great benefit to those suffering from disease.

EXAMPLES

Example 1

Preparation of Cinnamic Acid-Based Oligomers

Three cinnamic acid derivatives, caffeic acid, ferulic acid and sinapic acid, were chosen for homo-polymerization primarily due to their ability to hydrogen bond, form ionic interactions and undergo sulfation. HRP-catalyzed oxidation of these monomers generates radical intermediates, (see FIG. 1), which couple with monomers to give β-O-4- and β-5- linked dimeric units. These units undergo chain extension with radicals, such as the β-O-4- and β-5-linked oligomer radicals shown in FIG. 1, to give DHPs. Simultaneously, side reactions, such as decarboxylation, may occur to give variant oligomers.

The dehydrogenation polymers (DHP) were prepared by the so-called "zutropfverfahren" procedure consisting of slow addition of a phenylpropenoid precursor and $H_2O_2$ to a solution of horseradish peroxidase (HRP). Briefly, 4-hydroxycinnamic acid precursor (25 mM) in 10 mM sodium phosphate buffer, pH 8.0, (200 mL) and $H_2O_2$ (75 mM) in the same buffer (100 mL) were simultaneously added drop-wise over a 5 h period to a stirring solution of HRP (10 mg) in the sodium phosphate buffer (50 mL) at room temperature in dark. Three additional aliquots $H_2O_2$ (75 mM) were added over the next 72 h while monitoring the polymerization using analytical size-exclusion chromatography (SEC). At the end of nearly 80 hours, the solution was freeze-dried, the solid re-dissolved in deionized water, and the solution filtered repeatedly through a molecular membrane (Amicon YM5K) to remove salts and low molecular weight material. The final solution was washed with ether and lyophilized to give a dark brown powder, the sodium salt of the DHP.

The DHPs were judged to be heterogeneous through size-exclusion and reverse-phase chromatographies. The three DHPs were named CD, FD, and SD in the unsulfated form. The peak-average molecular weight ($M_P$) of CD, FD and SD was found to be 1,180, 2,480 and 1,190, respectively, while the number-average molecular weight ($M_N$) was 880, 1,870, and 1,020, respectively, suggesting unsymmetrical distribution of higher and lower molecular weight chains. The weight-average molecular weight ($M_W$) was found to be 2,800, 3,650, and 2,990, respectively, indicating that on average these oligomers are reasonably similar. The average oligomer is estimated to be between 4-13-mer for CD, 8-15-mer for FD, and 4-11-mer for SD.

The unsulfated DHPs were sulfated using $Et3N:SO_3$ complex. The lyophilized DHP sample (500 mg) was dissolved in dry DMF (50 mL) containing triethylamine-sulfur trioxide complex (1 g) and stirred for 24 h at 60° C. After the removal of most of the DMF in vacuo, the remaining product was taken up in 30% aqueous sodium acetate, the sodium salt precipitated using ~10 volume of cold ethanol. The precipitated product was further purified with dialysis using Amicon 10K cutoff dialysis membrane. Sulfated DHPs are named CDSO3, FDSO3 and SDSO3. The C, H, and O composition of the three classes of DHPs is listed in Table 1. The sulfur proportion in the sulfated DHPs remains fairly consistent in the range of 4.4 to 5.3%, which corresponds to the presence of nearly 1 sulfate group every 2.5-3.3 monomers (Table 1).

TABLE 1

Average molecular weight, elemental composition and sulfate density of DHPs

| Average Molecular Weight[a] | | | | Elemental Composition[f] | | | | |
|---|---|---|---|---|---|---|---|---|
| $M_P$[b] (Da) | $M_N$[c] (Da) | $M_W$[d] (Da) | Size[e] | C (%) | H (%) | O (%) | S (%) | Sulfates per Unit[g] |
| 1,180 | 880 | 2,800 | 5-13 | 54.8 (61.0)[h] | 3.5 (3.0) | 39.2 (36.0) | — | — |
| 2,480 | 1,870 | 3,650 | 8-15 | 61.9 (62.8) | 4.3 (3.8) | 33.6 (33.4) | — | — |
| 1,190 | 1,020 | 2,990 | 4-11 | 55.8 (59.7) | 4.2 (4.2) | 38.0 (36.1) | — | — |
| —[i] | — | — | — | 46.1 (49.6) | 4.0 (2.2) | 36.7 (38.1) | 5.3 (5.9) | ~0.40 |
| — | — | — | — | 52.4 (54.1) | 4.6 (3.1) | 35.1 (35.3) | 4.4 (4.3) | ~0.30 |
| — | — | — | — | 45.8 (50.4) | 4.0 (3.4) | 39.0 (37.8) | 4.5 (4.9) | ~0.38 |

[a]Average molecular weight was obtained through non-aqueous SEC on the acetylated derivatives, $CD_{AC}$, $FD_{AC}$, and $SD_{AC}$, using polystyrene as standards. The error in determination of these numbers is less than 10%.
[b]Peak-average molecular weight.
[c]Number-average molecular weight.
[d]Weight-average molecular weight.
[e]Size of an average oligomer.
[f]Analysis was performed on unsulfated or sulfated DHPs, and not on acetylated DHPs.
[g]Average number of sulfates per monomeric unit was calculated from elemental sulfur composition and the size of an average unsulfated oligomer.
[h]numbers in brackets shows the predicted composition of a homogeneous β-O-4-linked decamer of appropriate DHP.
[i]not determined.

Prolongation of Clotting Time:

Prothrombin and activated partial thromboplastin time (PT and APTT) reflect the activity of the extrinsic and intrinsic pathways of coagulation and thus, are measures of the anticoagulation state of the plasma. PT and APTT were measured with citrated human plasma at six to eight concentrations of unsulfated and sulfated DHPs.

Clotting time was determined in a standard 1-stage recalcification assay with a BBL Fibrosystem fibrometer (Becton-Dickinson, Sparles, Md.). For PT assays, thromboplastin was reconstituted according to manufacturer's directions and warmed to 37° C. A 10 µL sample of the DHP, to give the desired concentration, was brought up to 100 µL with citrated human plasma, incubated for 30 s at 37° C. following by addition of 200 µL pre-warmed thromboplastin. Clotting time in the absence of an anticoagulant was determined using 10 µL deionized water. For APTT assay, 10 µL DHP sample was mixed with 90 µL citrated human plasma and 100 µL of pre-warmed APTT reagent (0.2% ellagic acid). After incubation for 220 s, clotting was initiated by adding 100 µL, of 25 mM $CaCl_2$ (37° C.) and time to clot noted. Each clotting assay was performed in duplicate or triplicate. The data were fit to a quadratic function, which was used to determine the concentration of DHP (or the reference molecules) necessary to double the clotting time, 2×APTT or 2×PT.

All samples showed considerable concentration-dependent prolongation of clotting time characterized by a rapid increase in time to clot. The anticoagulant activity is typically defined in terms of the concentration of the anticoagulant needed for doubling the normal plasma clotting time. A 2-fold increase in prothrombin time required plasma concentration of unsulfated DHPs in the range of 98-212 µg/mL (Table 2). This concentration decreased to 42-105 µg/mL, or nearly 2-3-fold lower, for sulfated DHPs. In contrast, for the reference molecule, LMWH (from Sigma), a two-fold increase in PT was found to require 142 µg/mL.

In a similar manner, doubling of APTT required ~25-40 µg/mL and ~13-23 µg/mL of unsulfated and sulfated DHPs, respectively. In contrast, the LMWH brought about 2×APTT at 5.9 µg/mL. These results suggest that unsulfated DHPs are less potent than their sulfated counterparts. In addition, a trend is discernible. Except for APTT with unsulfated DHPs, CD appears to be consistently more potent than FD, which in turn is better than SD and this trend holds for their sulfated derivatives.

Assuming homogeneous CD, FD and SD preparations with $M_W$ of 2,800, 3,650, and 2,990, respectively (Table 2), ~35-71 µM and ~15-35 µM of unsulfated and sulfated oligomers, respectively, would be needed for 2×PT. These concentrations change to 9-11 µM and 5-8 µM, respectively, for a doubling of APTT. The LMWH ($M_W$=5,060) gives values of 28 µM and 1.2 µM for 2×PT and 2×APTT, respectively. Thus, the concentration of DHPs, especially sulfated DHPs, required to double PT are similar to LMWH, while for doubling of APTT ~3-10-fold more sulfated DHPs are required.

TABLE 2

Anticoagulation effect of DHP's from 4-hydroxycinnamic acid

| | Clotting Time[a] | | $IC_{50}$[b] | | | |
|---|---|---|---|---|---|---|
| DHP | 2 × PT (µg/mL) | 2 × APTT (µg/mL) | fXa (µg/mL) | fXa w/ AT (µg/mL) | T (µg/mL) | T w/ AT (µg/mL) |
| CD | 98.1 ± 0.7 | 24.9 ± 2.3 | 0.4 ± 0.1[c] | —[d] | 0.19 ± 0.03 | — |
| FD | 161.3 ± 2.7 | 39.5 ± 0.8 | 2.7 ± 0.3 | — | 1.16 ± 0.06 | — |
| SD | 212.0 ± 2.9 | 32.1 ± 1.5 | 2.8 ± 0.9 | — | 1.00 ± 0.04 | — |
| $CD_S$ | 42.1 ± 0.3 | 13.0 ± 5.0 | 0.11 ± 0.01 | 0.19 ± 0.01 | 0.07 ± 0.01 | 0.20 ± 0.02 |
| $FD_S$ | 63.4 ± 0.1 | 18.3 ± 1.9 | 0.32 ± 0.04 | 0.56 ± 0.02 | 0.12 ± 0.01 | 0.31 ± 0.02 |
| $SD_S$ | 104.6 ± 3.9 | 22.6 ± 1.1 | 0.84 ± 0.08 | 0.37 ± 0.01 | 0.33 ± 0.01 | 0.16 ± 0.01 |
| LMWH | 142.1 ± 3.6 | 5.9 ± 3.0 | — | 0.037 ± 0.003 | — | 0.011 ± 0.001 |
| PAA | 4259 ± 40 | —[d] | No Inh.[e] | No Inh. | No Inh. | No Inh. |
| (+)-CS | 927[f] | 284[f] | —[d] | — | — | — |

[a]PT and APTT values were deduced in in vitro human plasma experiments where the clot initiator is either thromboplastin or ellagic acid, respectively. Experiments were performed in duplicate or triplicate. Errors represent ± 1 S.E.
[b]$IC_{50}$ values were determined through direct inhibition of thrombin or factor Xa using a chromogenic substrate hydrolysis assay.
[c]S.E. ± 1
[d]Not determined.
[e]No inhibition was observed in buffer containing $Ca^{2+}$ at concentrations lower than 4560 µg/mL.
[f]Experiment performed only once.

Inhibition Factor Xa and Thrombin in the Absence of Antithrombin:

The initial results on inhibition of thrombin and factor Xa in the presence and absence of antithrombin suggested the possibility of a dual inhibition mechanism. The discovery of a direct inhibition mechanism was unexpected and hence interesting. To better define this initial observation, inhibition of thrombin and factor Xa by sulfated DHPs was studied under pseudo-first order conditions in the absence of human plasma antithrombin.

Direct inhibition of thrombin, factor Xa, factor IXa, and FVIIa by sulfated DHPs was determined using chromogenic substrate hydrolysis assays. For these assays, 10 µL DHP at concentrations ranging from 0.035 to 10,000 µg/mL was diluted with 930 µL of the appropriate buffer in PEG 20,000-coated polystyrene cuvettes. The buffers used in these experiments include 20 mM Tris-HCl buffer, pH 7.4, containing 100 mM NaCl, 2.5 mM $CaCl_2$ and 0.1% polyethylene glycol (PEG) 8000 for thrombin and factor Xa; 100 mM HEPES buffer, pH 8, containing 100 mM NaCl and 10 mM $CaCl_2$ for factor IXa; and 25 mM HEPES buffer, pH 7.4, containing 100 mM NaCl and 5 mM $CaCl_2$ for factor VIIa. Following the preparation of the sulfated DHP solution, 10 µl, of the proteinase solution was added to give 1 to 10 nM initial enzyme concentration and the cuvette incubated for 10 minutes. Thrombin, factor Xa and factor VIIa assays were incubated at 25° C., while factor IXa assays were incubated at 20° C. Following incubation, 50 µL of 2 mM chromogenic substrate, Spectrozyme TH, FXa, FVIIa or Spectrozyme FIXa, was rapidly added and the residual enzyme activity was determined from the initial rate of increase in absorbance at 405 nm. Relative residual proteinase activity at each concentration was calculated using the activity measured under otherwise identical conditions, except for the absence of the sulfated DHP. Logistic equation I was used to fit the dose-dependence of residual proteinase activity to obtain $IC_{50}$.

$$Y = Y_O + \frac{Y_M - Y_O}{1 + 10^{(\log[DHP]_O - \log IC_{50})HS}}$$ Equation 1

In this equation Y is the ratio of residual proteinase activity in the presence of inhibitor to its absence (fractional residual activity), $Y_M$ and $Y_O$ are the maximum and minimum possible values of the fractional residual proteinase activity, $IC_{50}$ is the concentration of the inhibitor that results in 50% inhibition of enzyme activity, and HS is the Hill slope.

Figure 2A:
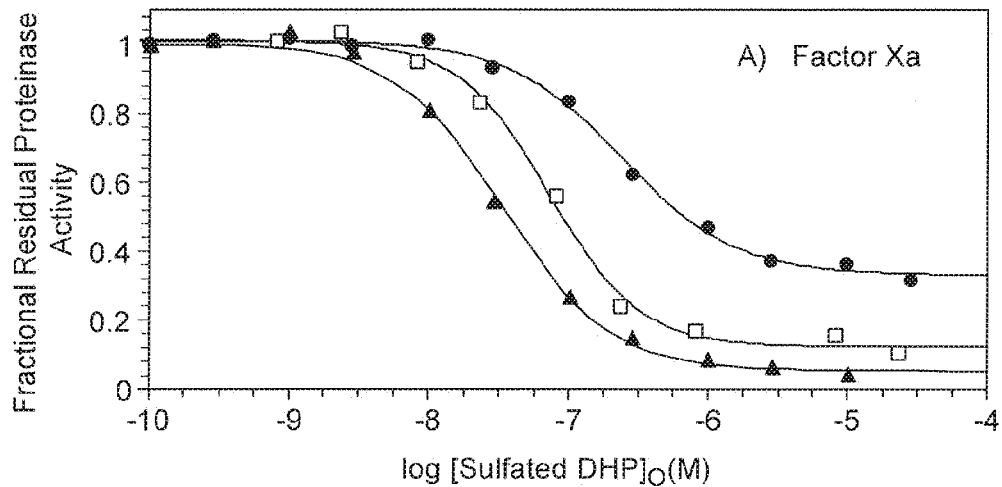
FIGS. 2A and B Inhibition of A, Factor Xa and B, Thrombin in the absence of antithrombin. ●=SDSO3; ▲=CDSO3; □=FDSO3.
Figure 2B:
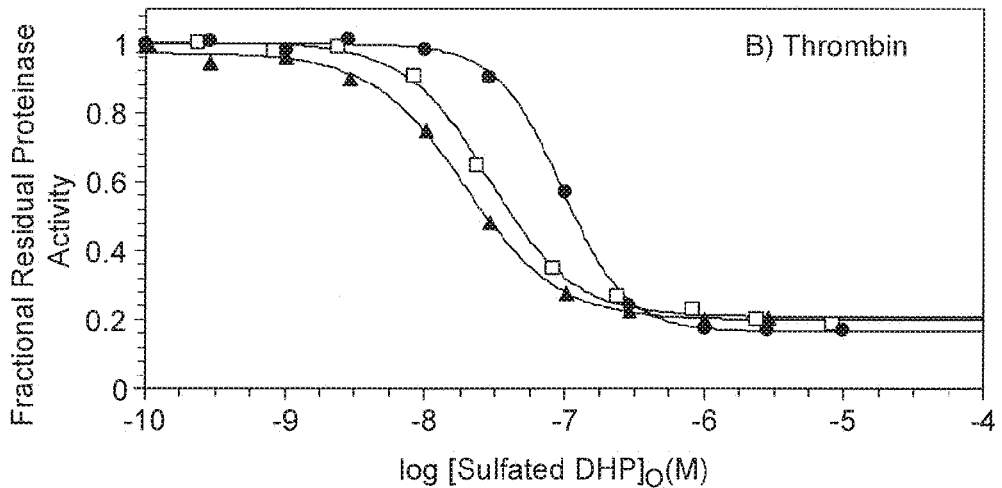

The inhibition of enzyme activity was followed by spectrophotometric determination of the initial rate of hydrolysis of appropriate chromogenic substrate. As the concentration of the sulfated DHP was increased, the residual factor Xa or thrombin activity progressively decreased (see FIGS. 2A and B). In contrast, enoxaparin and fondaparinux, two sulfated molecules known to activate antithrombin, displayed no direct inhibition of thrombin and factor Xa even at concentrations higher than 100 µM (not shown). The decrease in enzyme activity by sulfate DHPs was fitted by the logistic dose-response equation to derive the $IC_{50}$ value, the concentration of the inhibitor that results in 50% reduction in enzyme activity (Table 3). The three sulfated DHPs inhibited factor Xa and thrombin with $IC_{50}$ values in the range of 34-244 nM and 18-94 nM, respectively. Of the three sulfated DHPs, CDSO3 and FDSO3 are nearly 3.2-7.2-fold better than SDSO3. Thus, the sulfated DHPs studied here are potent direct inhibitors of factor Xa and thrombin.

To determine whether the sulfated DHPs inhibit other enzymes of the coagulation cascade directly, we studied inhibition of factor IXa and factor VIIa, enzymes of the intrinsic and extrinsic pathways, respectively. The inhibition was studied in a manner similar to that reported in the literature, except for the presence of sulfated DHPs (or reference LMWH) in the reaction mixture. CDSO3 and FDSO3 inhibited factor IXa with $IC_{50}$ values of 3.4 and 0.5 while inhibition of factor VIIa was not detectable (Table 3). SDSO3 was essentially inactive against both factor IXa and factor VIIa at concentrations as high as 28 µM (not shown). These results suggest that CDSO3 and FDSO3 are better direct inhibitors of factor Xa and thrombin with 7-99-fold and 17-187-fold, respectively, higher selectivity over factor IXa. The level of selectivity of direct inhibition against factor VIIa is even greater (>319-fold).

TABLE 3

Inhibition parameters for sulfated DHPs and enoxaparin inhibiting coagulation enzymes in the absence of antithrombin.

| Proteinase | Parameter | CDSO3 | FDSO3 | SDSO3 | Enoxaparin |
|---|---|---|---|---|---|
| Thrombin | $IC_{50}$ (nM) | 18 ± 2[b] | 29 ± 2 | 94 ± 4 | >222,222[c] |
|  | HS | 1.27 ± 0.20 | 1.43 ± 0.22 | 1.87 ± 0.24 | n/a |
|  | $Y_M$ | 0.97 ± 0.02 | 1.00 ± 0.02 | 1.00 ± 0.02 | — |
|  | $Y_O$ | 0.20 ± 0.02 | 0.21 ± 0.02 | 0.17 ± 0.02 | — |
| Factor Xa | $IC_{50}$ (nM) | 34 ± 5 | 74 ± 8 | 244 ± 28 | No Inh.[d] |
|  | HS | 1.11 ± 0.16 | 1.34 ± 0.30 | 1.07 ± 0.18 | — |
|  | $Y_M$ | 1.03 ± 0.02 | 1.01 ± 0.04 | 1.01 ± 0.02 | — |
|  | $Y_O$ | 0.06 ± 0.02 | 0.12 ± 0.04 | 0.33 ± 0.02 | — |
| Factor IXa | $IC_{50}$ (nM) | 3380 ± 64 | 492 ± 16 | >28500[c] | No Inh. |
|  | HS | 1.16 ± 0.24 | 0.73 ± 0.30 | n/a | n/a |
|  | $Y_M$ | 1.00 ± 0.02 | 1.03 ± 0.06 | — | — |
|  | $Y_O$ | 0.04 ± 0.08 | 0.30 ± 0.12 | — | — |
| Factor VIIa | $IC_{50}$ (nM) | >29,000[c] | >23,640 | >28,500 | — |
|  | HS | n/a | n/a | n/a | — |
|  | $Y_M$ | — | — | — | — |
|  | $Y_O$ | — | — | — | — |

[a]The $IC_{50}$, HS, $Y_M$, $Y_O$ values were obtained following non-linear regression analysis of direct inhibition of factor Xa, thrombin, factor IXa and factor VIIa at pH 7.4 and 25° C. The inhibition assays were performed in appropriate buffers through spectrophotometric measurement of residual proteinase activity following incubation of the enzyme and the inhibitors for a fixed time period of 10 minutes.
[b]Errors represent ± 2 S.E.
[c]Estimated values based on the highest concentration of the anticoagulant used in the experiment.
[d]No inhibition was observed.

Figure 3A:
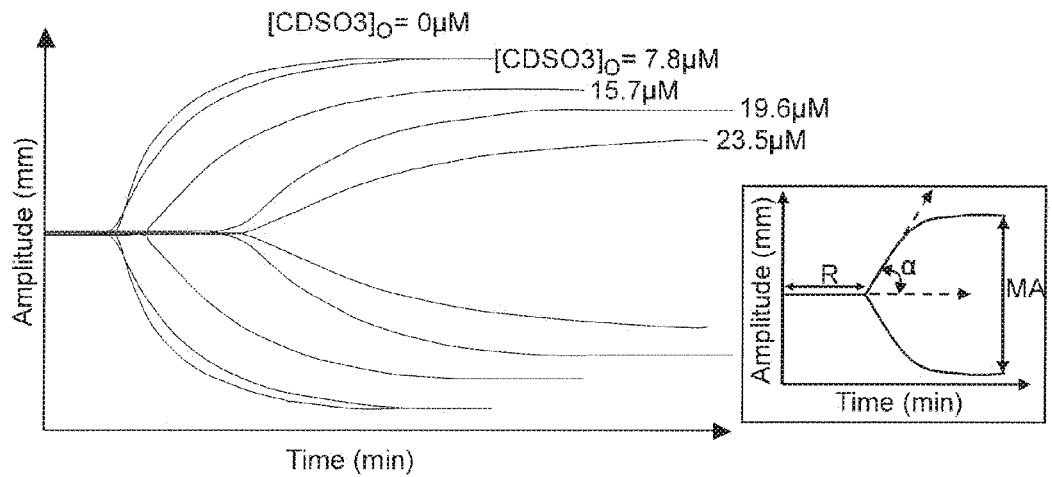
FIGS. 3A and B. Thromboelastographic measurement of effect of sulfated dehydropolymers (DHPs) on whole blood clotting. A, amplitude, B, shear elastic modulus.
Figure 3B:
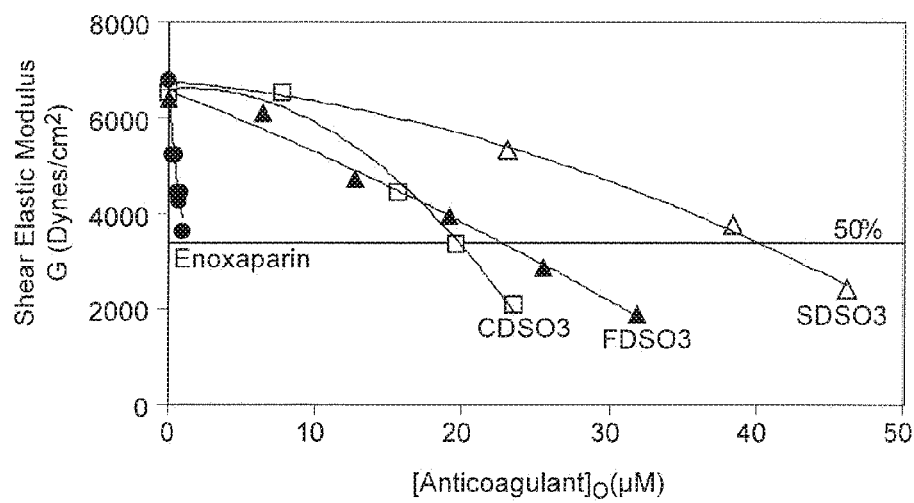

Thromboelastographic Measurement of Effect of Sulfated DHPs on Whole Blood Clotting:

Whole blood clotting is a dynamic process that involves many components including cells, which may alter anticoagulant potency. To compare sulfated DHPs and enoxaparin in a whole blood system, we employed thromboelastography (TEG®), a technique used in clinical settings for following anticoagulation with LMWHs. TEG® measures various responses of a formed clot to shearing force. In this technique, a pin is inserted into an oscillating cup containing whole blood. As fibrin polymerizes, the pin starts to move with the oscillating cup and the movement of the pin is recorded as amplitude, which in time reaches maximum amplitude (MA) (see FIGS. 3A and B). The stronger the clot, the more the pin moves with the cup and the higher the MA. Shear elastic modulus strength (G), a measure of clot stiffness, is calculated from MA. Additionally reaction time R and angle a are also obtained in a TEG® experiment. R is the time required for the initial fibrin formation, while a is the acute angle in degrees between an extension of the R tracing and the tangent of the maximum slope produced by the TEG® tracing during clot stiffening. Angle a is a measure of the rate of formation of three-dimensional fibrin network. Parameters that affect MA include fibrin concentration and structure, concentration and functional state of platelets, deficiency of coagulation factors and presence of clotting inhibitors.

All three sulfated DHPs affect R, a, MA and G parameters in a dose-dependent manner (Table 4). Briefly, as the concentration of CDSO3 increases from 0 to 24.3 µM, R increases from 7.0 to 21.5 min. This effect parallels the time to clot results obtained in the plasma assay. Likewise, sulfated DHPs lower the value of angle a from 59° for normal blood to 13.5-17° at the highest concentrations studied. This indicates that the kinetics of fibrin polymerization and networking is significantly retarded by the presence of sulfated DHPs. Enoxaparin exhibits similar characteristics, except that it is 23-51-fold more potent than sulfated DHPs when comparisons are made at doubling the R value from its value in the absence of any anticoagulants. Likewise, enoxaparin is 17-32-fold and 18-37-fold more potent when comparisons are made for a 50% reduction in the angle a and shear elastic modulus G, respectively.

TABLE 4

Parameters obtained from thromboelastograph (TEG ®) study of sulfated DHPs and enoxaparin in human whole blood.[a]

| | Conc (µM) | R[b] (min) | α[c] (degrees) | MA[d] (mm) | G[e] (Dynes/cm$^2$) |
|---|---|---|---|---|---|
| Blank | 0 | 7.0 | 59.0 | 56.5 | 6456.5 |
| CDSO3 | 8.1 | 7.0 | 49.5 | 56.5 | 6494.5 |
| | 16.2 | 10.5 | 38.0 | 47.0 | 4434.0 |
| | 20.3 | 19 | 27.0 | 40.0 | 3333.5 |
| | 24.3 | 21.5 | 15.0 | 29.5 | 2092.0 |
| FDSO3 | 6.5 | 7.0 | 60.0 | 55.0 | 6111.0 |
| | 13.0 | 11.5 | 43.5 | 48.5 | 4708.5 |
| | 19.6 | 13.5 | 34.5 | 44.0 | 3928.5 |
| | 26.1 | 14.0 | 22.5 | 36.5 | 2874.0 |
| | 32.7 | 19.0 | 13.5 | 27.5 | 1896.5 |
| SDSO3 | 22.8 | 8.5 | 50.5 | 51.5 | 5309.5 |
| | 38.0 | 13.0 | 26 | 43 | 3772.0 |
| | 45.6 | 21.0 | 17.0 | 32.5 | 2407.5 |
| Enoxaparin | 0.3 | 8 | 49 | 51 | 5204.0 |
| | 0.44 | 9.5 | 39.5 | 51 | 5204.0 |
| | 0.6 | 11.5 | 43.0 | 47.0 | 4434.0 |
| | 0.75 | 14.0 | 41.0 | 46 | 4259.5 |
| | 0.89 | 17.0 | 36.5 | 47.0 | 4434.0 |
| | 1.0 | 17.0 | 31.5 | 42.0 | 3620.5 |

[a]TEG parameters were obtained in an automated manner from the TEG ® coagulation analyzer. See Experimental Procedures for a description of the setup.
[b]Reaction time R is the time interval between the initiation of coagulation and the appearance of first detectable signal of no less than 2 mm in amplitude.
[c]Angle α is the acute angle in degrees between an extension of the R value tracing and the tangent of the maximum slope produced by the TEG ® tracing.
[d]Maximum amplitude (MA) is the maximum distance the pin of TEG ® moves at the end.
[e]The shear elastic modulus strength (G) is a calculated parameter (G = 5000 × MA/(100 − MA) and is a measure of clot strength.

Effect of Sulfated DHPs on Whole Blood Coagulation as Evaluated by Hemostasis Analysis System.

To further compare the whole blood anticoagulant potential of the sulfated DHPs with enoxaparin, we performed an ex-vivo study using HAS™, which measures the forces generated by platelets within a clot. In this technique, the clot is allowed to form between a temperature-controlled lower surface (cup) and a parallel upper surface (cone). As the clot grows, it attaches to both the surfaces pulling the fibrin strands inward. This pull is measured by a displacement transducer, which produces an electrical signal on the cone proportional to the amount of force generated by the platelets. HAS™ also provides detailed information on clot structure through the measurement of clot elastic modulus (CEM), which is the ratio of stress induced by platelets to strain arising from the change in clot thickness. PCF is observed to increase as soon as thrombin is formed suggesting that appearance of PCF can be used as surrogate marker for TGT (thrombin generation time), the minimal time required for production of thrombin following initiation of clotting.

In addition to its dependence on thrombin, PCF is sensitive to platelet number, platelet metabolic status, presence of thrombin inhibitors and degree of GPIIb/IIIa exposure. Likewise, CEM is a complex parameter that is sensitive to changes in clot structure, fibrinogen concentration, the rate of thrombin generation and red blood cell flexibility, while TGT is sensitive to clotting factor deficiencies, antithrombin concentration and presence of anticoagulants. Low PCF and low CEM coupled with a prolonged TGT are associated with increased bleeding risk, while elevated PCF and CEM paired with a decreased TGT are associated with thrombotic disease states.

Analysis of platelet function and clot structure was performed using the HAS™ (Hemodyne, Inc., Richmond, Va.). A mixture of 700 µl of citrated whole blood and 10 µl sulfated DHP or ddH$_2$O (control) was co-incubated at room temperature for 5 minutes and then 700 µl was placed in a disposable cup. To initiate clotting, 50 µl of 150 mM CaCl$_2$ was added to 700 µl of the blood-DHP mixture to give a final CaCl$_2$ concentration of 10 mM, while the cone was simultaneously lowered into the recalcified blood sample. As the clotting proceeds, platelets attach to both surfaces generating tension within the fibrin meshwork. This tension is measured with a displacement transducer in terms of platelet contractile force (PCF). The onset of PCF is a measure of thrombin generation time (TGT), while clot elastic modulus (GEM) is the ratio of the applied force (stress) by the transducer to the measured displacement (strain). The HAS™ system operates in an automated manner until all data is collected.

Figure 4A:
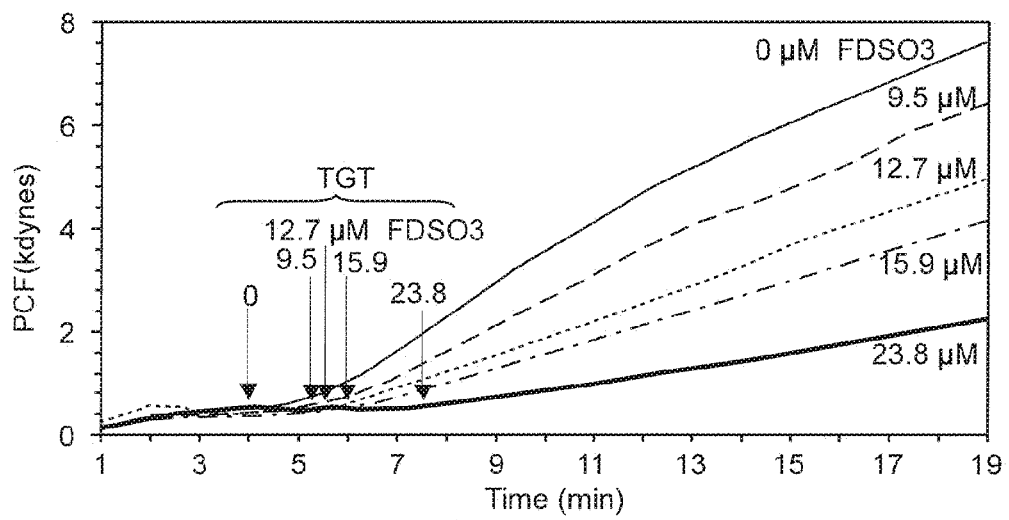
FIG. 4A-C. Effect of sulfated DHPs of whole blood coagulation as evaluated by hemostasis analysis system. A, platelet contractile force (PCF) vs time; B, PCF vs anticoagulant; C, clot elastic modulus (CEM) vs anticoagulant.
Figure 4B:
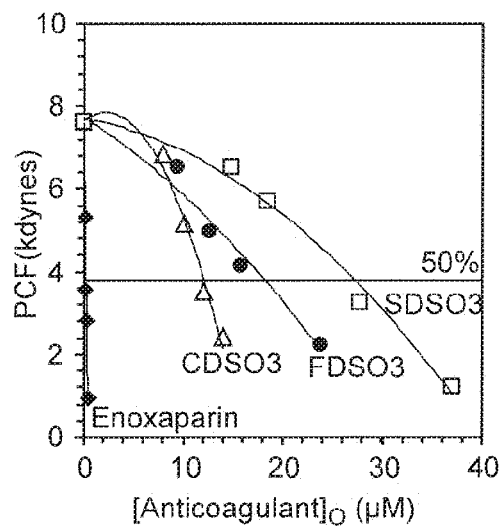
Figure 4C:
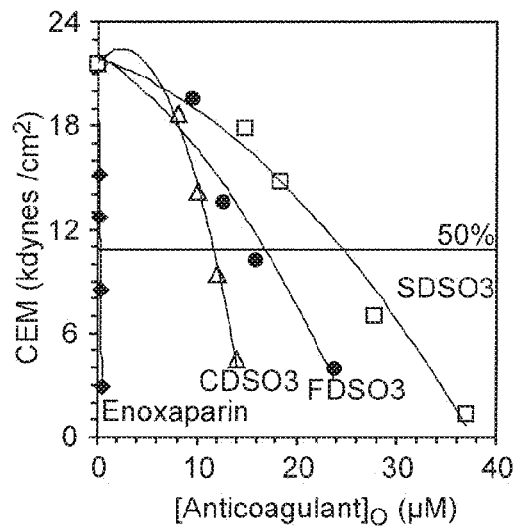

All three DHPs affect TGT, PCF and CEM parameters in a dose-dependent manner. For example, as the concentration of FDSO3 increases from 0 to 23.8 µM, the TGT value increases from 235 seconds to 465 seconds (see FIGS. 4A and B). This effect parallels the results obtained in the plasma thrombogenesis assay and TEG®. More importantly, the presence of sulfated DHPs in blood decreases PCF from 7.6 Kdynes to 2.4-1.2 Kdynes at 14-37 µM, while enoxaparin induces a PCF of 0.9 Kdynes at 0.44 µM. When comparisons are made for a 50% reduction in PCF, enoxaparin is 63-140-fold more potent. Likewise, sulfated DHPs decrease CEM from 21.6 Kdynes/cm$^2$ for normal blood to 4.5-1.3 Kdynes/cm$^2$ at the highest concentrations studied. Comparison of CEM values indicates that enoxaparin is 43-90-fold more potent than sulfated DHPs. These results confirm that sulfated DHPs behave in a manner similar to enoxaparin, except for the concentration at which these are effective.

Example 2

Identification of High Affinity Anti-Coagulant Oligomers

Specific molecules in the mixture of oligomers were found to be the primary cause of anticoagulant activity. These specific molecules include certain β-O4 trimers and tetramers and selected β-5 tetramer.

Figure 5:
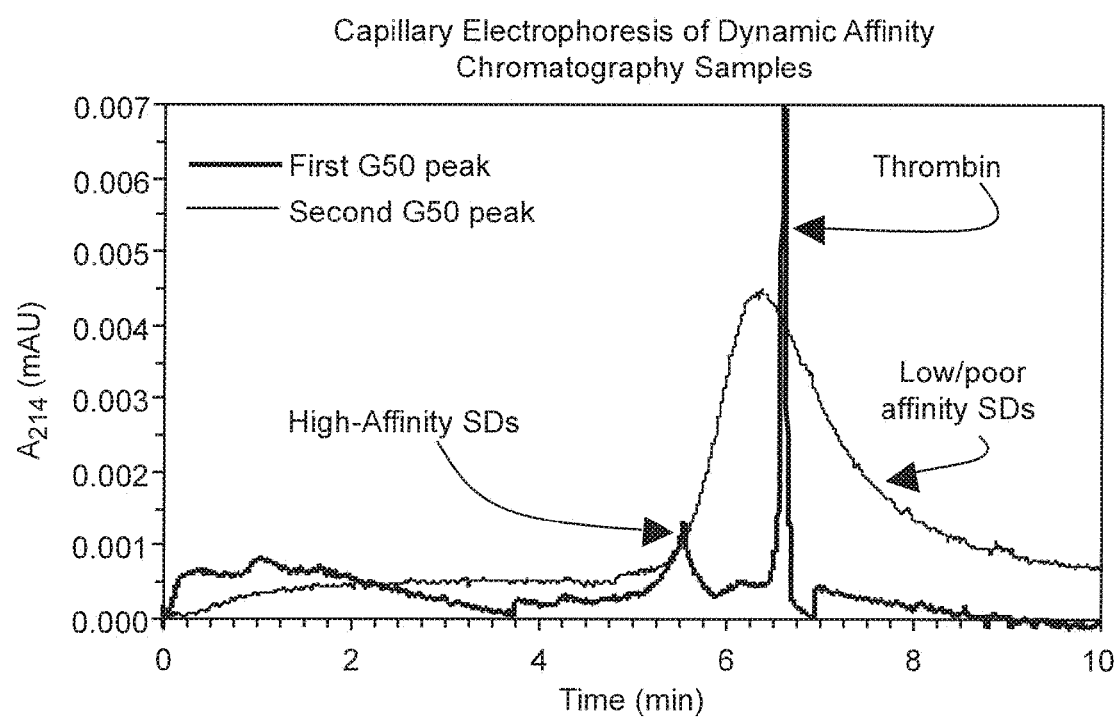
FIG. 5. Capillary electrophoresis of dynamic affinity chromatography samples.

To isolate specific structures that are the seat of anticoagulant activity, dynamic thrombin affinity chromatography was performed. Dynamic affinity chromatography was performed by size-based separation of a pre-formed complex of thrombin and FDSO3 on a G50 column using sodium phosphate buffer, pH 7.4, containing 250 mM NaCl. SEC gave two peaks. The first peak corresponded to FDSO3-thrombin complex, while the second was due to FDSO3 alone. Reverse polarity capillary electrophoresis (CE) at 8 kV of the first G50 peak in the presence of 0.1% sodium dodecyl sulfate showed the presence of 1) FDSO3 between 5.2 and 5.7 min corresponding to the high-affinity sub-population and 2) thrombin between 6.5 and 6.7 min (see electropherograms in FIG. 5). The second G50 peak, which is the population that did not bind thrombin (no thrombin found in this sample), showed a much broader peak in CE (see electropherograms in FIG. 5) closely matching the CE profile of the starting mixture. It is important to note that the high-affinity sub-population isolated through affinity chromatography migrates fastest in the reverse polarity CE suggesting that these sequences contain higher negative charge density (—COO$^-$ & —OSO$_3^-$) than the rest of the population.

Figure 6:
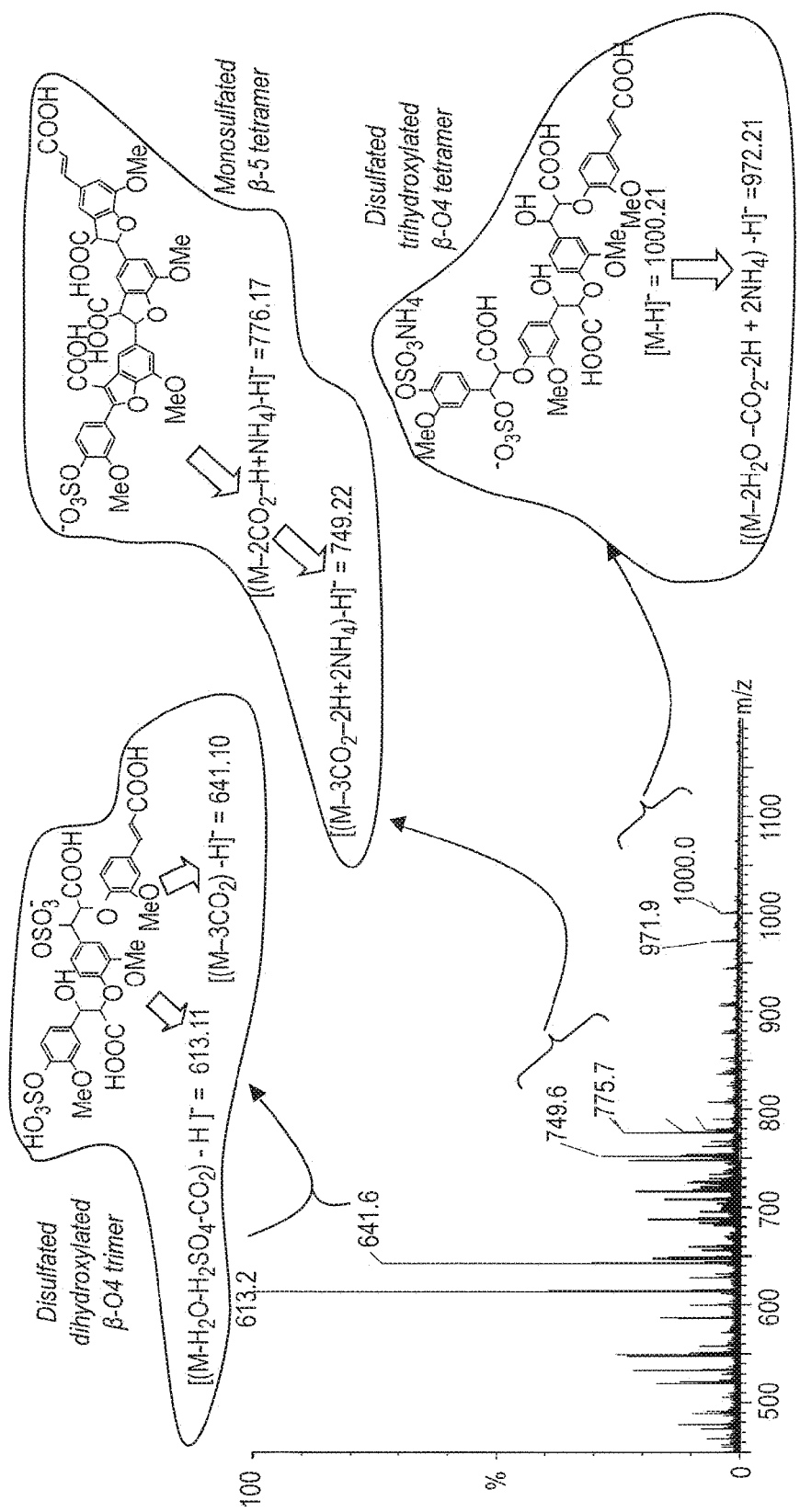
FIG. 6. Negative mode ESI-mass spectroscopy spectrum of the first peak obtained from G50 dynamic affinity chromatography of FDSO3-thrombin complex.
Figure 7A:
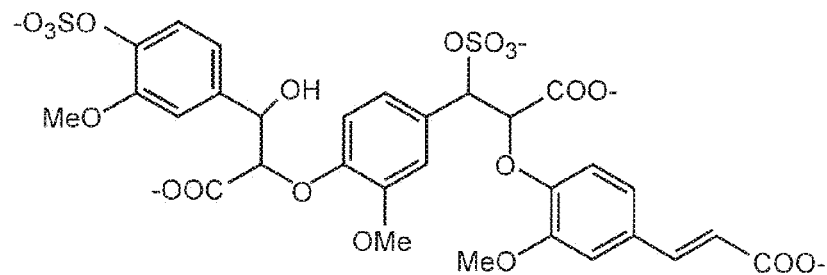
FIG. 7A-D. Structures of sulfated and hydroxylated β-O4 and β-5 FDSO3 trimers and tetramers identified by ESI-MS to bind thrombin with high affinity. A, disulfated, monohydroxylated β-O4 trimer; B, monosulfated, trihydroxylated β-O4 tetramer; C, monsulfated β-5 trimer; C, monsulfated tetramer.
Figure 7B:
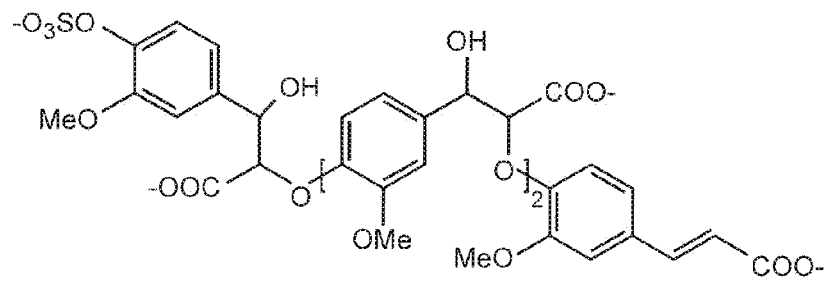
Figure 7C:
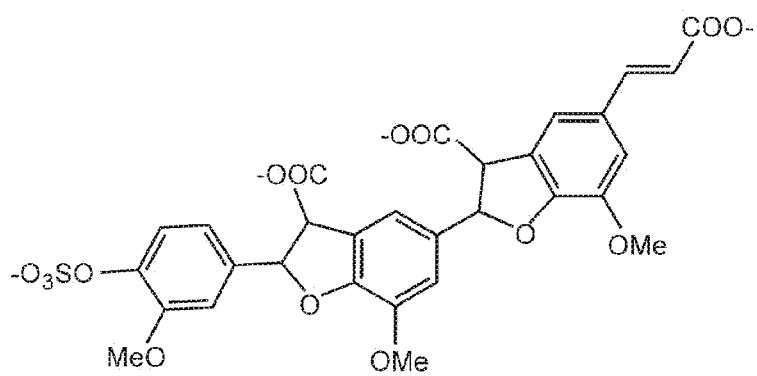
Figure 7D:
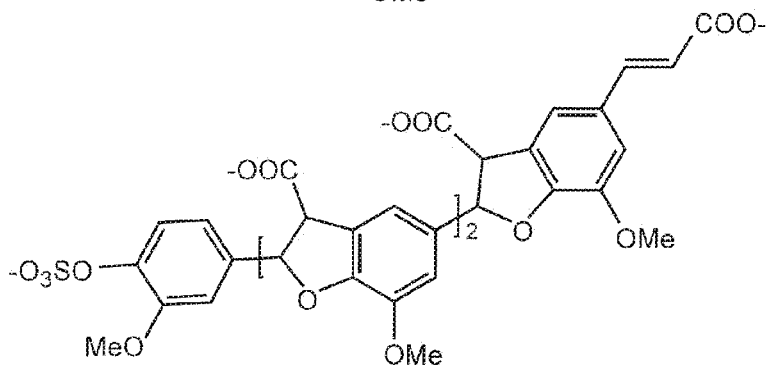

The identification of structures that constitute the high affinity fraction (peak 1 in G50) was performed through negative ion ESI-MS analysis. The spectrum of this sub-population displayed several peaks in the 500-1000 m/z region (see FIG. 6). Theoretically, more than 2000 [M-H]$^-$ species can arise from β-O4 and β-5 oligomers (dimer→tetramer) sequences. From the possible [M-H]$^-$ species, the observed ESI-MS spectrum can be explained by three groups of peaks in the 600, 700 and 900 m/z region corresponding to disulfated dihydroxylated β-O4 trimer, monosulfated β-5 tetramer and disulfated trihydroxylated β-O4 tetramer structures, respectively (shown within balloons in the FIG. 6). It is important to note that despite a large number of possible [M-H]$^-$ species, the peaks can be uniquely assigned to structures because of the power of MS.

To further confirm these structures the HAF fraction was dialyzed against 20 mM ammonium acetate buffer, pH 5.0, overnight and lyophilized to prepare sample for ESI-MS analysis. The structures of the high affinity molecules identified are as shown in FIGS. 7A-D. These structures confirm the earlier assignment and show that the sulfated and hydroxylated β-O4 and β-5 trimers and tetramers possess high affinity for thrombin, and possibly factor Xa, and are expected to possess potent anticoagulant activity.

Example 3

Oligomers as Elastase Inhibitors, Anti-Inflammation Agents and Anti-Oxidants

The oligomers were tested for their ability to inhibit elastase, as anti-inflammation agents and as anti-oxidants.

In Vitro Elastase Inhibition:

Inhibitory activity of each of the oligomers to human neutrophil elastase (HNE; 40 U/mg; Athens Research & Technology) was determined by chromogenic substrate hydrolysis assay at 37° C. in a 96-well plate format. Enzymatic degradation of 0.2 mM N-methoxysuccinyl Ala-Ala-Pro-Val p-nitroanilide (Sigma-Aldrich) by 24 mU/ml HNE was monitored for 2 h in the presence of each oligomer at 0-100 μM. The absorbance at 405 nm due to p-nitroaniline (pNA) generation was measured with a multi-mode microplate reader (Synergy 2; BioTek Instruments) and converted to the pNA mass. Initial linear rate of the substrate degradation was assessed with the pNA mass generated for the first 10 min. The IC$_{50}$ values were derived from nonlinear regression curve-fitting, assuming the sigmoidal concentration-dependence of the initial rate with a logistic function equation.

In Vitro Lung Cell Anti-Inflammation:

Anti-inflammatory activity of each of the oligomers was determined using Calu-3 human bronchial epithelial cells (American Type Culture Collection; ATCC), from repression of the inflammatory transcription factor NFκB. The Calu-3 cells of 0.5×10$^6$ cells/cm$^2$ in 12-well plates were cultured for 24 h and then, transfected with 0.6 μg luciferase (Luc)-tagged reporter plasmid construct of NFκB (pNFκB-Luc) for another 24 h using the Effectene reagents (Qiagen) under the protocol optimized in-house. On day 3, the transfected Calu-3 cells were stimulated for 6 h with 30 ng/ml human tumor necrosis factor α (TNF α; BD Biosciences) in the presence of each oligomer at 0-100 μM in culture. Then, the Calu-3 cells were lysed, after which the Luc activities were measured using 20/20n luminometer (Turner BioSystems). The cellular NFκB-Luc activity was expressed in relative light unit/mg protein, normalized by the total protein measured by the BCA assay (Pierce Biotechnology). A fold-induction of such a normalized NFκB-Luc activity relative to the transfection control was derived for treatment group comparison; this accommodated inter-transfection efficiency differences.

In Vitro Anti-Oxidative Activity:

Anti-oxidative activity of the oligomers was determined at room temperature using the chemical antioxidant assay kit (Cayman Chemical Co.) in a 96-well plate format, in accord with the manufacturer's protocol. The kit has been validated in-house with respect to assay precision and accuracy. Oxidative reaction of ABTS (2,2'-azino-di-[3-ethylbenzthiazoline sulphonate]) to its oxidative product, ABTS•+, by met-myoglobin and 84 μM hydrogen peroxide were monitored for 20 min in the presence of each oligomer at 0-100 μM. The absorbance at 750 nm due to ABTS•+ generation was measured using the microplate reader. Initial linear rate of oxidation was assessed with the absorbance produced for the first 5 min. The half maximal anti-oxidative concentration (AOC$_{50}$) values were derived, assuming the sigmoidal concentration-dependence of the initial oxidation rate in the logistic function equation.

Results

Sulfated Caffeic Acid Oligomer (CDS) is a Potent Human Neutrophil Elastase (HNE) Inhibitor.

Figure 8:
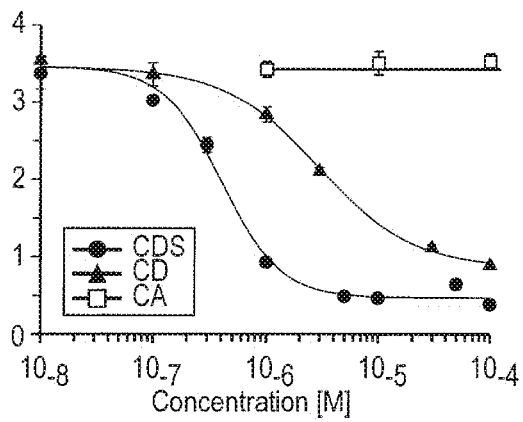
FIG. 8. p-Nitroaniline (pNA) generated for 10 minutes as a function of CDS, CD or CA concentration in the in vitro chromogenic substrate human neutrophil elastase (HNE) hydrolysis assay. Data: means±SD from n=3.

FIG. 8 shows the p-nitroaniline (pNA) generation in the first 10 min by FINE in the presence of CA, CD (the unsulfated oligomer) and CDS at various concentrations in the in vitro chromogenic substrate hydrolysis assay. While the monomer, CA, failed to inhibit HNE by 100 μM, the oligomers, CD and CDS, exhibited concentration-dependent HNE inhibition at 0.1-100 μM. As summarized in Table 5, the IC$_{50}$ value for the sulfated oligomer, CDS, was derived to be 0.40±0.04 μM, which was 7.3-fold more potent than the unsulfated counterpart, CD (IC$_{50}$=2.92±0.38 μM). Hence, these HNE inhibitory activities resulted from the repeated structure of CA, rather than the single unit activity, and there was a greater benefit of sulfation for the enhanced activity. This benefit of sulfation was similarly observed in the anti-coagulation potency (described above), attributed in part to an increased negative charge (i.e., —OSO$_3$—) density of CDS, compared to CD. Meanwhile, the other 2 sulfated oligomers, FDS and SDS, resulted in less potent HNE inhibitory activities than CDS, yielding the IC$_{50}$ values of 0.59±0.05 μM and 0.63±0.15 μM, respectively (Table 5); this, in turn, has demonstrated that the most potent unit structure is caffeic acid among these cinnamic acids. However, all three species have activities that may be clinically significant. Finally, CDS did not inhibit PPE by 0.1 mM (data not shown), demonstrating its relative specificity to HNE.

TABLE 5

In vitro IC$_{50}$ values of CA, CD CDS, FDS and SDS to HNE.

| Molecule | IC$_{50}$ |
|---|---|
| CA | NA |
| CD | 2.92 ± 0.38 |

TABLE 5-continued

In vitro $IC_{50}$ values of CA, CD CDS, FDS and SDS to HNE.

| Molecule | $IC_{50}$ |
|---|---|
| CDS | 0.40 ± 0.04 |
| FDS | 0.59 ± 0.05 |
| SDS | 0.63 ± 0.15 |

NA = not applicable

Sulfated Caffeic Acid Oligomer (CDS) Exhibits Lung Epithelial Anti-Inflammation.

Figure 9:
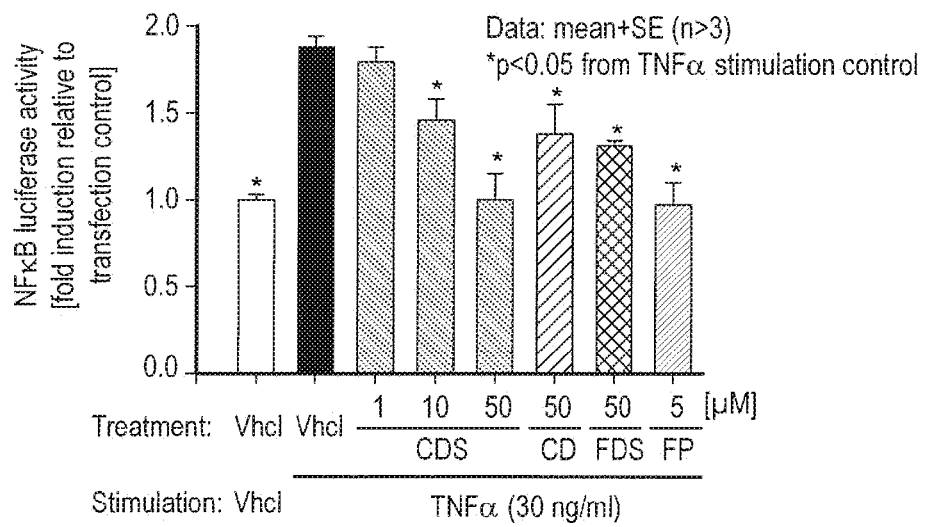
FIG. 9. TNFα-dependent NFκB-Luc activities of the Calu-3 cells in the absence or presence of various test molecules including fluticasone propionate (FP) Vhcl: vehicle.

FIG. 9 shows the TNFα-dependent NFκB luciferase (Luc) activities of the Calu-3 epithelial cells in the absence or presence of various oligomers or fluticasone propionate (FP). The NFκB-Luc activity shown as the fold-induction relative to the transfection control represented the Calu-3 epithelial cell inflammation. CDS exhibited concentration-dependent repression against the 1.9-fold increased NFκB-Luc activity by TNFα. Its $IC_{50}$ value was estimated to be ~10 μM, given its 47.7 and 100% repression at 10 and 50 μM, respectively. Notably however, while both were somewhat effective, neither CD nor FDS enabled such a complete repression at 50 μM, suggesting that CDS was again the most potent in this anti-inflammation among these molecules. Meanwhile, in this system, FP, one of the most potent inhaled corticosteroids used in the treatment of asthma, was capable of causing 100% repression at the lower 5 μM, as shown in FIG. 9. This supported a notion that the anti-inflammatory activity of CDS was slightly lower than that for the most potent FP, yet still remarkable, especially as its monomer, CA, had no appreciable repression by 100 μM in this system (data not shown).

Sulfated Caffeic Acid Oligomer (CDS) is a Potent Antioxidant.

Figure 10:
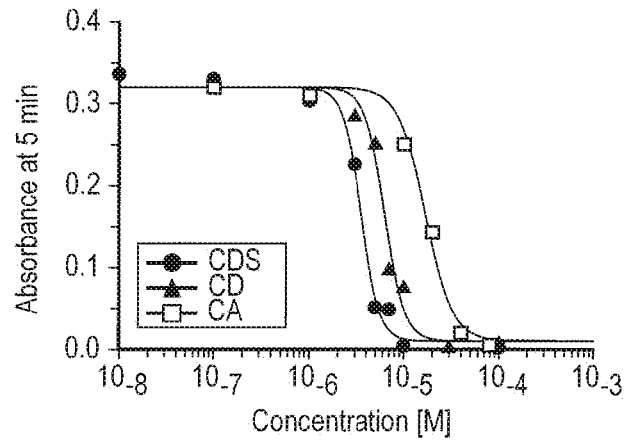
FIG. 10. Absorbance at 750 nm generated for 5 minutes as a function of CDS, CD or CA concentration in the chemical antioxidant assay. Data: means from n=2 or 3.

FIG. 10 shows the absorbance at 750 nm generated for the first 5 min by chromogenic substrate oxidation in the presence of CA, CD and CDS at various concentrations in the in vitro chemical antioxidant assay. Consistent with the literature, the monomer, CA, exhibited moderate antioxidant activity, yielding the half maximal anti-oxidative concentration ($AOC_{50}$) value of 16.8±1.6 μM, as summarized in Table 6. This antioxidant activity was enhanced apparently by 5-13 units of oligomerization, as CD resulted in a 2.7-fold lower $AOC_{50}$ value of 6.25±0.51 μM (Table 6). However, unlike elastase (HNE) inhibition, its sulfation caused only 1.8-fold increase in the potency, yielding the $AOC_{50}$ value of 3.51±0.18 μM for CDS (Table 6). It was likely therefore that caffeic acid (CA) and its repeated structure was a primary pharmacophore for this antioxidant activity, which was only slightly improved by the sulfation. In this context, the other two sulfated oligomers, FDS and SDS, showed only slightly lower activities than CDS, yielding their $AOC_{50}$ values of 5.13±0.51 μM and 5.92±0.86 μM, respectively (Table 6). While this rank-order of the oligomers was consistent with that of the monomers, these anti-oxidative potencies ($AOC_{50}$=3.5-6.3 μM) were equivalent to 0.3-0.5 mM of Trolox®, a tocopherol analogue known to have an intermediate anti-oxidative potency between vitamins C and E. Hence, the oligomers were much more potent antioxidants than these natural vitamins.

TABLE 6

In vitro $AOC_{50}$ values of CA, CD, CDS, FDS and SDS.

| Molecule | $AOC_{50}$ |
|---|---|
| CA | 16.8 ± 1.6 |
| CD | 6.25 ± 0.51 |
| CDS | 3.51 ± 0.18 |
| FDC | 5.13 ± 0.51 |
| SDS | 5.92 ± 0.86 |

These in vitro studies demonstrate that the sulfated caffeic acid oligomer (CDS) exhibited the most potent triple actions of HNE inhibition, lung epithelial anti-inflammation and anti-oxidation, yielding 0.40, ~10 and 3.51 μM of the half maximal effective concentrations, respectively. Its unsulfated oligomer (CD) and the sulfated oligomers of the other 2 cinnamic acids (FDS and SDS) were shown to be less potent in all inhibitory activities.

Example 4

Sulfated Caffeic Acid Oligomer (CDS) Prevents Airway Luminal Neutrophilia and Airspace Enlargement in the Rat Model of Pulmonary Emphysema Following Pulmonary Administration The ability of sulfated caffeic acid oligomer (CDS) to prevent symptoms of pulmonary emphysema was investigated in vivo using a rat model of human sputum elastase/cigarette smoke extract (HSE/CSE)-induced experimental pulmonary emphysema. Pulmonary emphysema was induced by a single orotracheal solution (0.2 ml) instillation of 360 U/kg HSE (Elastin Products Co.) and 100% CSE (freshly prepared) into the lungs of Sprague-Dawley rats (250-275 g). A Liquid MicroSprayer (Penn-Century) was used for instillation and thus inserted orotracheally through the glottis until its tip reached just before the tracheal bifurcation, and 0.2 ml solution of HSE/CSE was administered as a coarse solution spray under isoflurane anesthesia.

The triple inhibitor oligomer, CDS, was also administered to the lungs of the emphysema-induced rats via orotracheal solution (0.1 ml) instillation using the Liquid MicroSprayer by the method described above. The oligomer was administered to the lung at 30 μg/kg 2 h prior to HSE/CSE instillation ("prophylactic" protocol) Each group was comprised of 6-7 animals, among which 4-5 and 2 animals were sacrificed 48 h and 28 days post-HSE/CSE instillation, respectively, for the assessments described below.

At 48 h following HSE/CSE instillation, bronchoalveolar lavage (BAL) was carried out with 4-5 animals in each group. The animals were first perfused with saline under intraperitoneal 50 mg/kg pentobarbital anesthesia (Ovation Pharmaceuticals) and sacrificed by exsanguination. BAL was then performed on the whole lung lobes with 8 ml of ice-cold saline via 3-times of repeated wash. The BAL fluid (BALF) was centrifuged at 4,500 g for 5 min at 4° C., and the cell pellets were re-suspended in 1 ml saline; an aliquot was used to determine the total cell counts with a hemocytometer (Fisher). Differential cell counts, specifically for neutrophils and macrophages, were performed with the BAL cell smears from $0.04 \times 10^6$ cells in 0.1 ml saline prepared from the re-suspended samples via cytocentrifugation (Shandon Cytospin 2; Thermo Scientific) and Wright's stain (EMD Chemicals). A total of 300 leukocytes were counted under the microscope (BX40; Olympus America). The number of each cell type in the 8-ml BALF was calculated from the product of its fraction in the 300 cells and the total cell count obtained above. Meanwhile, at 28 days following HSE/CSE instillation, 2 rats in each group were sacrificed by exsanguination under intraperitoneal pentobarbital anesthesia. Immediately, 8-10 ml of 0.5% agarose (Fisher) solution at 45° C. was slowly introduced into the entire lung lobes through trachea under a hydrostatic pressure of 20 cm $H_2O$. The trachea and lung lobes were removed and placed in ice to solidify the luminally-filled agarose for over 10 min and then subjected to 24 h tissue fixation in 10% buffered formalin phosphate (Fisher) at 4° C. The 4 μm-thick lung lobar specimens were prepared from the paraffin-embedded blocks, followed by hematoxylin-eosin staining. The airspace area was quantified under a microscope (25× magnification; Olympus) by counting alveolar intercepts in a total of 12 fields and calculating the mean linear intercept (MLI) for each lung lobe, according to Thurlbeck [Thurlbeck WM. 1967. Internal surface area and other measurements in emphysema. Thorax 22:483-496.].

Results

Figure 11A:
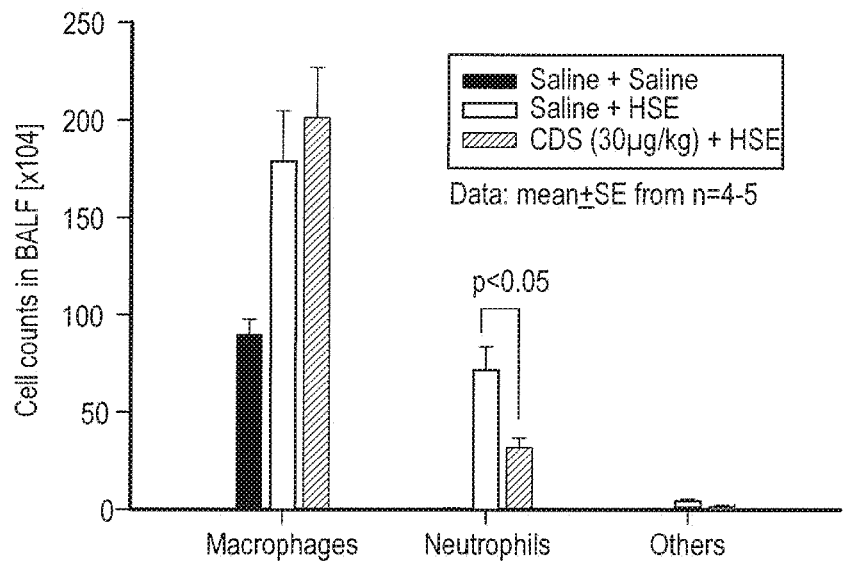
FIGS. 11A and B. A, differential cell counts in the bronchoalvelolar lavage fluid (BALF) and B, representative micrographs for the airspace enlargement assessments and their mean linear intercept (MLI) values (mean±SD from 12-field measurements), obtained from different treatment groups of the rat emphysema model.
Figure 11B:
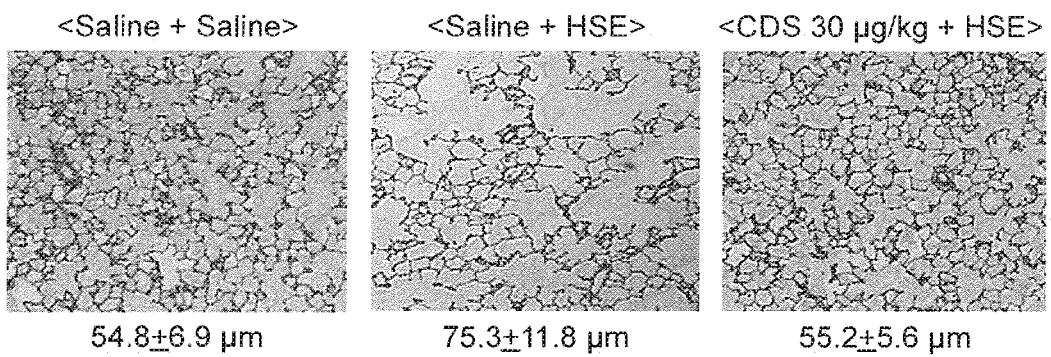

FIGS. 11A and B shows the results, suggesting potent in vivo protective effects of CDS administered to the lung. As can be seen in FIG. 11A, HSE/CSE was shown to induce airway luminal infiltration of macrophages and neutrophils at 48 h by 2.0- and 75.2-fold. While the number of the BALF macrophages remained statistically unchanged (p>0.05), the 75.2-fold induced neutrophils were shown to be reduced by 55.4% in response to CDS administration to the lung at 30 μg/kg. Meanwhile, as shown in FIG. 11B, HSE/CSE was shown to cause significant airspace enlargement (p<0.05) by 28 days, represented by a visual lack of certain alveolar walls as well as a 1.4-fold increase in their mean linear intercept (MLI; 54.8±6.9 μm→75.3±11.8 μm). Notably, this enlargement was not observed almost completely, when CDS was administered to the lung at 30 μg/kg, resulting in the MLI value of normal 55.2±5.6 μm. These results provide strong evidence that CDS, shown to be effective in vitro in EXAMPLE 3, is also effective in this in vivo animal model of emphysema. It should be noted finally that animals exhibited no abnormality in daily food and water intake and body weight gain as well as in appearance, posture and mobility for 28 days following CDS administration.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A cinnamic acid-based oligomer with a structure as represented in Formula 1

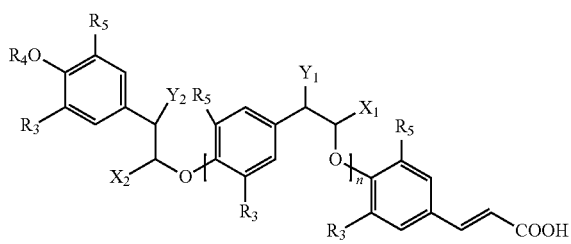

Formula 1 wherein
$R_3$=—OH or —OCH$_3$;
$R_4$=—H or —SO$_3^-$M$^+$ where M$^+$=an organic or inorganic cation;
$R_5$=—H or —OCH$_3$;
$X_1$ and $X_2$=—H or —COOH;
$Y_1$ and $Y_2$=—H or —OH or —SO$_3^-$M$^+$ where M$^+$=H$^+$ or an organic or inorganic cation; and n=1 or 2;
and wherein linkages between monomers of said cinnamic acid-based oligomer are β-O4 linkages;
or stereo-isomers thereof.

2. The cinnamic acid-based oligomer of claim 1, wherein said cinnamic acid-based oligomer is a trimer.

3. The acid-based oligomer of claim 2, wherein said cinnamic acid-based oligomer is

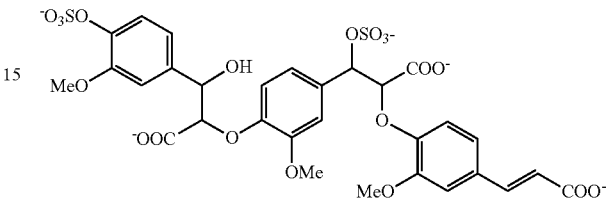

where the negative charges are within ionic bonding distance of H$^+$ or an organic or inorganic cation.

4. The cinnamic acid-based oligomer of claim 1, wherein said cinnamic acid-based oligomer is a tetramer.

5. The cinnamic acid-based oligomer of claim 4, wherein said cinnamic acid-based oligomer is

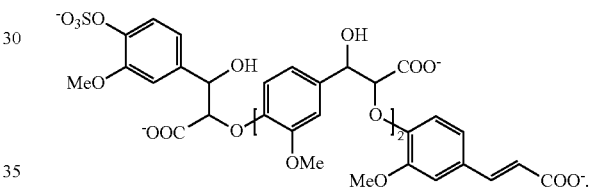

where the negative charges are within ionic bonding distance of H$^+$ or an organic or inorganic cation.

6. A method of inducing anti-coagulation in a patient in need thereof, comprising
administering to said patient
one or more cinnamic acid-based oligomers with a structure as represented in Formula 1

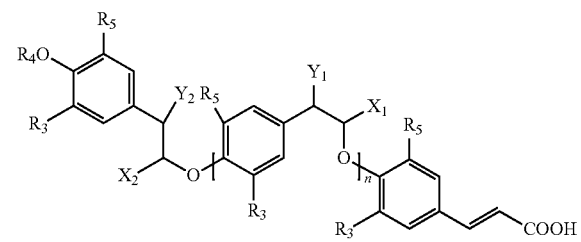

Formula 1 wherein
$R_3$=—OH or —OCH$_3$;
$R_4$=—H or —SO$_3^-$M$^+$ where M$^+$=an organic or inorganic cation;
$R_5$=—H or —OCH$_3$;
$X_1$ and $X_2$=—H or —COOH;
$Y_1$ and $Y_2$=—H or —OH or —SO$_3^-$M$^+$ where M$^+$=H$^+$ or an organic or inorganic cation; and n=1 or 2.

* * * * *